United States Patent
Zhang et al.

(10) Patent No.: US 10,766,901 B2
(45) Date of Patent: Sep. 8, 2020

(54) PREPARATION METHOD FOR CHIRAL PYRROLOPYRIMIDINE COMPOUND

(71) Applicants: CHIA TAI TIANQING PHARMACEUTICAL GROUP CO., LTD., Lianyungang, Jiangsu Province (CN); Lianyungang Runzhong Pharmaceutical Co., Ltd., Lianyungang, Jiangsu Province (CN); CENTAURUS BIOPHARMA CO., LTD., Beijing (CN)

(72) Inventors: Xiquan Zhang, Lianyungang (CN); Aiming Zhang, Lianyungang (CN); Zhou Zhou, Lianyungang (CN); Huadong Yao, Lianyungang (CN); Jie Xie, Lianyungang (CN)

(73) Assignees: CHIA TAI TIANQING PHARMACEUTICAL GROUP CO., LTD., Lianyungang, Jiangsu (CN); LIANYUNGANG RUNZHONG PHARMACEUTICAL CO., LTD., Lianyungang, Jiangsu (CN); CENTAURUS BIOPHARMA CO., LTD., Beijing (CN)

( * ) Notice: Subject to any disclaimer, the term of this patent is extended or adjusted under 35 U.S.C. 154(b) by 0 days.

(21) Appl. No.: 16/309,882

(22) PCT Filed: Jun. 15, 2017

(86) PCT No.: PCT/CN2017/088421
§ 371 (c)(1),
(2) Date: Dec. 13, 2018

(87) PCT Pub. No.: WO2017/215627
PCT Pub. Date: Dec. 21, 2017

(65) Prior Publication Data
US 2019/0211021 A1 Jul. 11, 2019

(30) Foreign Application Priority Data

Jun. 16, 2016 (CN) .......................... 2016 1 0432126

(51) Int. Cl.
C07D 487/04 (2006.01)
(52) U.S. Cl.
CPC ............ *C07D 487/04* (2013.01); *Y02P 20/55* (2015.11)

(58) Field of Classification Search
CPC .................................................. C07D 487/04
(Continued)

(56) References Cited

U.S. PATENT DOCUMENTS

2019/0201403 A1* 7/2019 Zhu .......................... A61P 35/00

FOREIGN PATENT DOCUMENTS

CN 101448826 A 6/2009
WO 1999065909 A1 12/1999
(Continued)

OTHER PUBLICATIONS

International Search Report in PCT/CN2017/088421, dated Sep. 21, 2017, 4 pages.
Elnagdi, et al. "Reactions with heterocyclic amidines VIII. Synthesis of some new imidazo [1, 2-b] pyrazole derivatives." Journal of Heterocyclic Chemistry 17, No. 1 (Jan. 1980): 73-76.
Extended European Search Report in EP17812738.7, dated Jan. 21, 2020.

(Continued)

*Primary Examiner* — Deepak R Rao
(74) *Attorney, Agent, or Firm* — Kilpatrick Townsend & Stockton LLP

(57) ABSTRACT

Provided are a preparation method for a chiral pyrrolopyrimidine compound and a related intermediate. In the method, a compound of formula A and a compound of formula 6 or a salt thereof are reacted to obtain a compound of formula 7 or a compound of formula 14, and a compound of formula I is prepared from the compound of formula 7 or the compound of formula 14. Also provided are the intermediate used, a preparation method for the intermediate and a use of the intermediate in the preparation of the compound of formula I. The preparation method has characteristics such as brief steps, a high stereoselectivity, a high utilization ratio of atoms, mild reaction conditions and a convenient post-treatment. The method avoids using an expensive asymmetric reaction catalyst, and is suitable for industrial production.

(Continued)

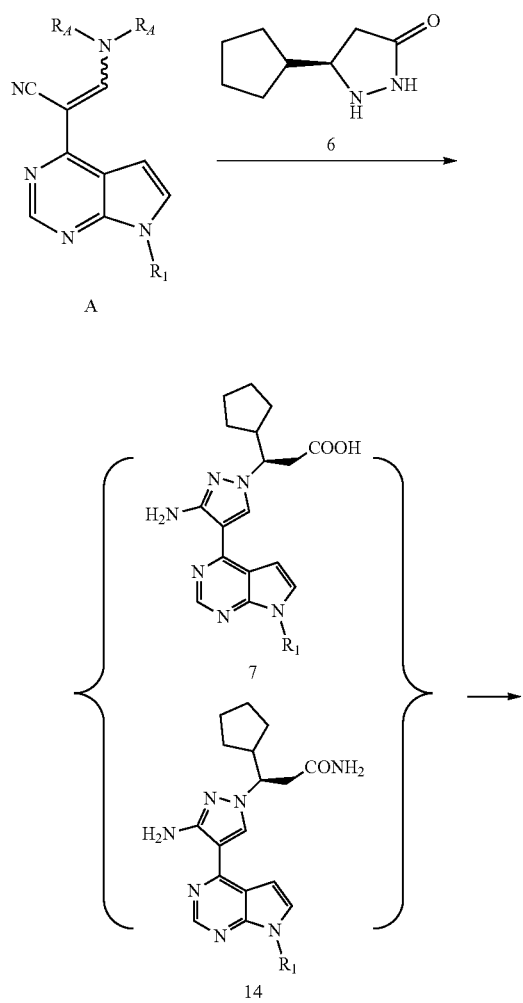

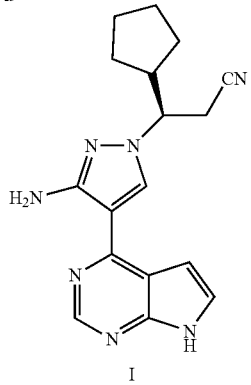

20 Claims, No Drawings

(58) Field of Classification Search
USPC .................................................. 544/280
See application file for complete search history.

(56) References Cited

FOREIGN PATENT DOCUMENTS

| WO | 2004100868 A2 | 11/2004 |
|---|---|---|
| WO | 2007070514 A1 | 6/2007 |
| WO | 2011028685 A1 | 3/2011 |
| WO | 2016/095805 A1 | 6/2016 |
| WO | WO 2016/095805 * | 6/2016 |

OTHER PUBLICATIONS

Hamamichi, Norimitsu, and Tadashi Miyasaka. "The synthesis of 6-C-substituted 9-methoxymethylpurine derivatives." Journal of heterocyclic chemistry 27, No. 4 (1990): 835-838.

* cited by examiner

PREPARATION METHOD FOR CHIRAL PYRROLOPYRIMIDINE COMPOUND

CROSS-REFERENCE TO RELATED APPLICATIONS

The present application is a U.S. National Stage Application of PCT/CN2017088421, filed Jun. 15, 2017, which claims the priority and benefit of Chinese Patent Application No. 201610432126.5 filed at the China National Intellectual Property Administration on Jun. 16, 2016, the entire content of which is incorporated herein by reference.

TECHNICAL FIELD

The present application belongs to the field of pharmaceutical synthesis, and specifically, the present application relates to a preparation method of a chiral pyrrolopyrimidine compound and a related intermediate.

BACKGROUND ART

Protein kinases (PKs), also called protein phosphokinases, are a sort of enzymes that catalyze the protein phosphorylation reaction. The protein kinases exert their physiological functions, including cell growth, survival and differentiation, organ formation and morphological change, neovascularization, tissue repair and regeneration, by catalyzing the phosphorylation of a protein. In addition to normal physiological functions, many protein kinases play an important role in human diseases (such as cancer). Cancerogenic protein kinases, i.e., a subgroup of protein kinases, when dysregulated, may cause tumor formation and growth, and further cause tumor metastasis and progression. To date, the cancerogenic protein kinases are one of the most important targets for treating cancers.

The protein kinases can be classified into receptor type and non-receptor type. A subfamily of the non-receptor type of tyrosine kinases (PTKs) comprises Janus kinase (JAK). As for the non-receptor type of tyrosine kinases, reference can be made in detail to, e.g., Bolen J B., Non receptor tyrosine protein kinases, Oncogene, 1993, 8(8): 2025-31.

Janus kinase (JAK) is a non-receptor type of tyrosine kinases (PTKs), which resides in cells and transduces cytokine stimulation signal via JAK-STAT pathway. By JAK-STAT pathway, a chemical signal outside the cell is transduced into a gene promoter on endonuclear DNA through cell membrane, and finally affects the DNA in cell to change its transcription and activity level. JAK-STAT pathway mainly consists of three components: (1) a receptor; (2) Janus kinase (JAK) and (3) a signal transducer and activator of transcription (STAT) protein. The receptor can be activated by interferon, interleukin, growth factor or other chemical messenger, and such activation leads to the phosphorylation of JAK itself. Then, the STAT protein bonds to the phosphorylated receptor, so that STAT is phosphorylated by JAK. After that, the phosphorylated STAT protein is isolated from the receptor, then dimerized and translocated into cell nucleus, thereby bonding to specific DNA site and changing transcription (Scott, M. J., C. J. Godshall et al. (2002). "Jaks, STATs, Cytokines, and Sepsis" Clin Diagn Lab Immunol 9(6): 1153-9).

JAK family plays a role in the cytokine-dependent regulation of proliferation and function of cells involved in immune response. At present, there are four known mammalian JAK family members: JAK1, JAK2, JAK3 and TYK2 (Tyrosine kinase 2). The JAK proteins have a size ranging from 120 kDa to 140 kDa, and comprise 7 conserved JAK homology (JH) domains. One of them is a functional catalytic kinase domain, and another is a pseudokinase domain which effectively exerts a regulatory function and/or acts as a docking site for STATs (Scott, Godshall et al. 2002, supra).

At present, various inhibitors for Janus kinase have been reported. The Chinese patent application No. 201410784461.2 filed on Dec. 16, 2014 discloses many JAK inhibitors, which is incorporated herein by reference in its entirety, including the compound (3R)-3-[3-amino-4-(7H-pyrrolo[2,3-d]pyrimidin-4-yl)-1H-pyrazol-1-yl]-3-cyclopentyl-propionitrile represented by the following formula I,

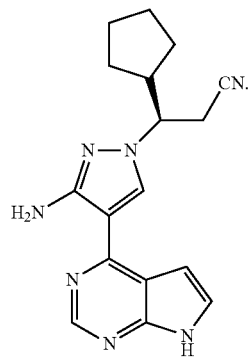

The compound of formula I is a chiral compound, and there is a need to develop a preparation method thereof having a high yield, high chiral purity and good atom economy.

SUMMARY OF THE INVENTION

In an aspect, the present application provides a method for preparing a compound of formula I, comprising reacting a compound of formula A with a compound of formula 6 or a salt thereof to obtain a compound of formula 7 or a compound of formula 14, and preparing the compound of formula I from the compound of formula 7 or the compound of formula 14:

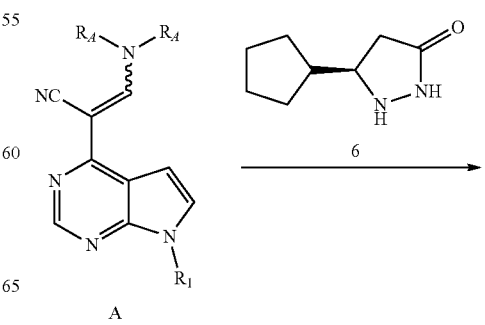

-continued

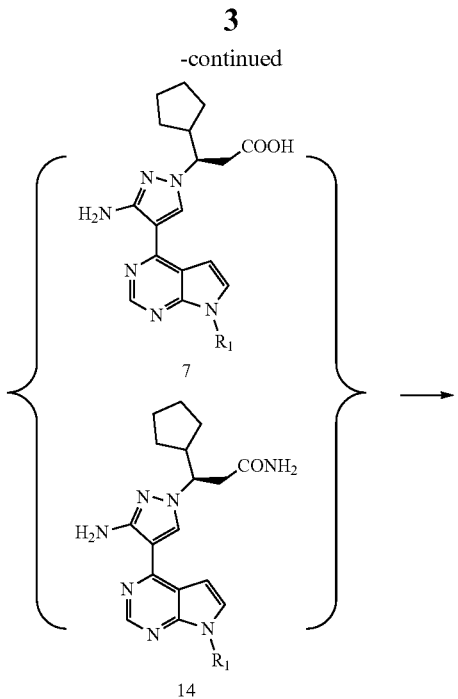

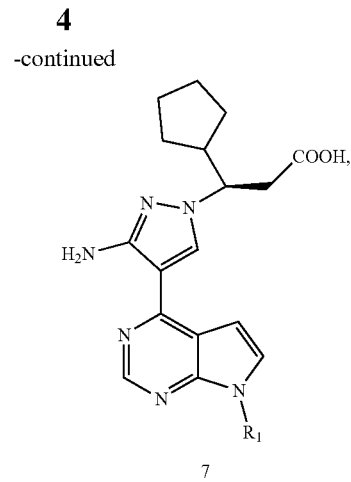

wherein $R_1$ is selected from the group consisting of H and an amino-protecting group.

In another aspect, the present application provides a method for preparing a compound of formula 14, comprising reacting a compound of formula 13 with a compound of formula 6 or a salt thereof to obtain the compound of formula 14:

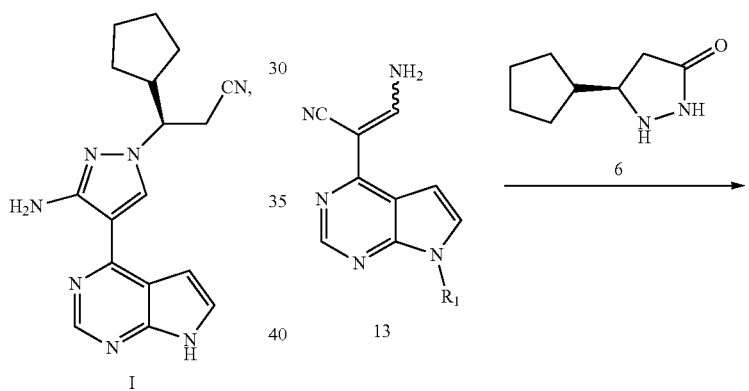

wherein $R_1$ is selected from the group consisting of H and an amino-protecting group; and $R_A$ is selected from the group consisting of H and $CH_3$.

In another aspect, the present application provides a method for preparing a compound of formula 7, comprising reacting a compound of formula 5 with a compound of formula 6 or a salt thereof to obtain the compound of formula 7:

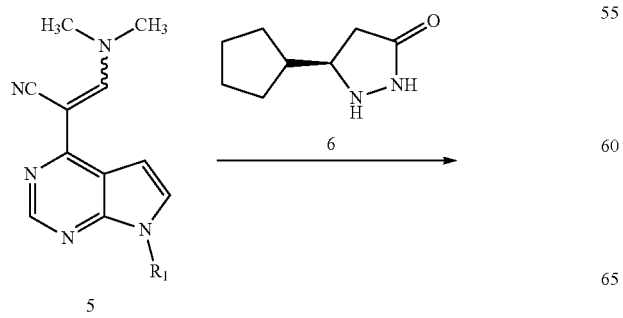

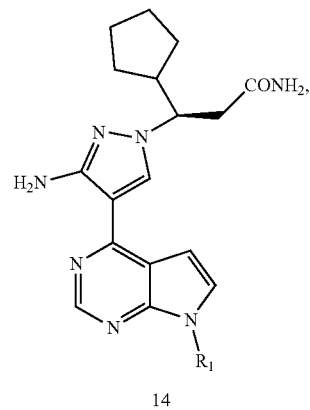

wherein $R_1$ is selected from the group consisting of H and an amino-protecting group.

In another aspect, the present application provides a use of a reaction of a compound of formula 5 and a compound of formula 6 or a salt thereof to obtain a compound of formula 7 in the preparation of a compound of formula I:

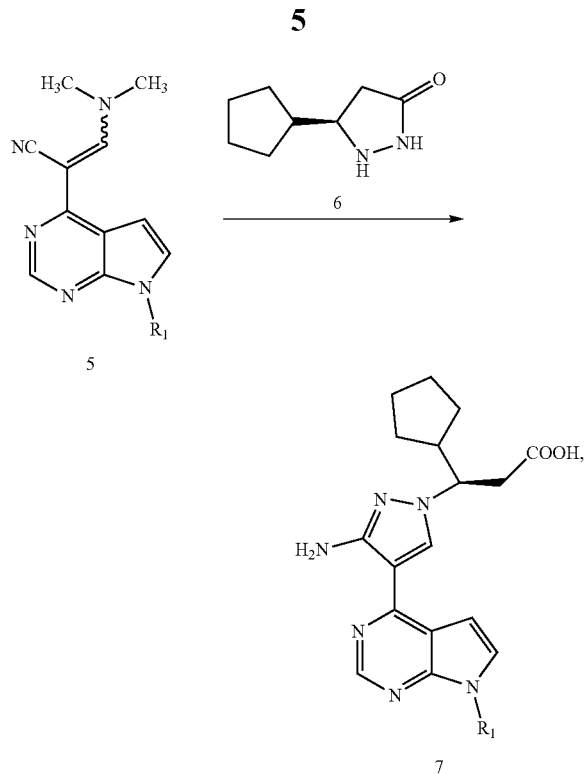

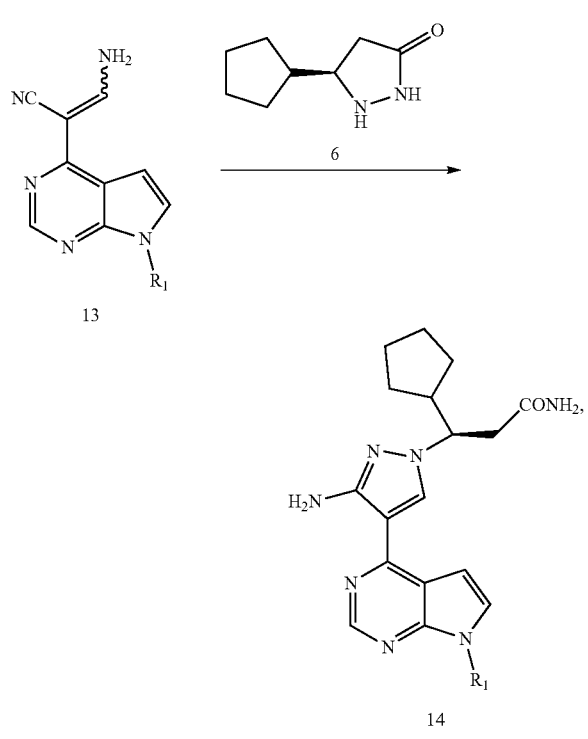

wherein R₁ is selected from the group consisting of H and an amino-protecting group.

In another aspect, the present application provides intermediates for preparing a compound of formula I and a use of the intermediates in the preparation of the compound of formula I:

wherein R₁ is selected from the group consisting of H and an amino-protecting group.

In another aspect, the present application provides a use of a reaction of a compound of formula 13 and a compound of formula 6 or a salt thereof to obtain a compound of formula 14 in the preparation of a compound of formula I:

wherein $R_1$ is selected from the group consisting of H and an amino-protecting group; $R_3$ is selected from the group consisting of H and acyclic imide-protecting group; and $R_4$ is selected from the group consisting of —COOH, —CONH₂, and —CN, with the proviso that if $R_4$ is —CN, then $R_1$ and $R_3$ are not both H.

DETAILED DESCRIPTION OF THE INVENTION

In an aspect, the present application provides a method for preparing a compound of formula I, comprising reacting a compound of formula A with a compound of formula 6 or a salt thereof to obtain a compound of formula 7 or a compound of formula 14, and preparing the compound of formula I from the compound of formula 7 or the compound of formula 14:

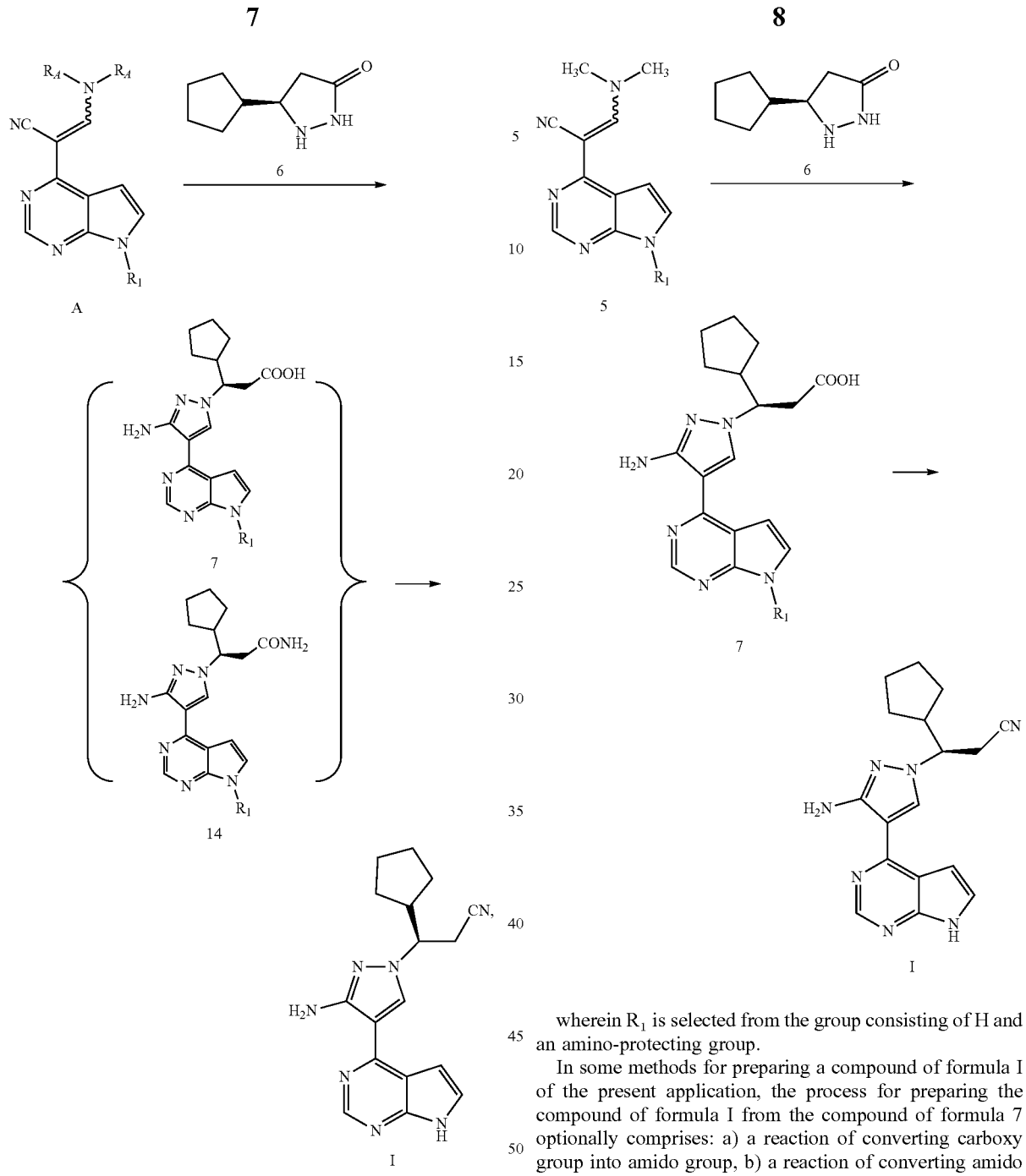

wherein $R_1$ is selected from the group consisting of H and an amino-protecting group; and $R_A$ is selected from the group consisting of H and $CH_3$.

Where $R_A$ is H, the compound of formula A reacts with the compound of formula 6 or a salt thereof to obtain the compound of formula 14; and where $R_A$ is $CH_3$, the compound of formula A reacts with the compound of formula 6 or a salt thereof to obtain the compound of formula 7.

In some embodiments of the present application, the method for preparing a compound of formula I comprises reacting a compound of formula 5 with a compound of formula 6 or a salt thereof to obtain a compound of formula 7, and preparing the compound of formula I from the compound of formula 7:

wherein $R_1$ is selected from the group consisting of H and an amino-protecting group.

In some methods for preparing a compound of formula I of the present application, the process for preparing the compound of formula I from the compound of formula 7 optionally comprises: a) a reaction of converting carboxy group into amido group, b) a reaction of converting amido group into cyano group, c) a reaction of linking amino group on a pyrazole ring with a protecting group, d) a reaction of removing the protective group of amino group on the pyrazole ring, and/or e) a reaction of removing $R_1$. The description manner of the aforementioned five reactions does not limit the occurrence order of these reactions. A person skilled in the art can change the occurrence order of the aforementioned five reactions according to the actual situation, or can combine two or more of the aforementioned reactions to occur simultaneously, both of which are within the protection scope of the present application.

In the process for preparing the compound of formula I from the compound of formula 7 of some methods for preparing a compound of formula I of the present application, optionally, the order of d) a reaction of removing the protective group of amino group on the pyrazole ring and e)

a reaction of removing $R_1$ can be that d) the reaction of removing the protective group of amino group on the pyrazole ring occurs prior to e) the reaction of removing $R_1$, or e) the reaction of removing $R_1$ occurs prior to d) the reaction of removing the protective group of amino group on the pyrazole ring, or d) the reaction of removing the protective group of amino group on the pyrazole ring and e) the reaction of removing $R_1$ occur simultaneously.

In the process for preparing the compound of formula I from the compound of formula 7 of some methods for preparing a compound of formula I of the present application, optionally, c) the reaction of linking amino group on a pyrazole ring with a protecting group occurs prior to a) the reaction of converting carboxy group into amido group, or c) the reaction of linking amino group on a pyrazole ring with a protecting group occurs prior to e) the reaction of removing $R_1$.

In some embodiments of the present application, where $R_1$ in the compound of formula 7 is an amino-protecting group, the process for preparing the compound of formula I from the compound of formula 7 comprises the following steps: (1) linking amino group on a pyrazole ring of the compound of formula 7 with a protecting group; (2) converting carboxy group of the compound obtained from step (1) into amido group; (3) converting amido group of the compound obtained from step (2) into cyano group; (4) removing the protective group of amino group on the pyrazole ring of the compound obtained from step (3), and (5) removing $R_1$ prior to step (1), after step (1) but prior to step (2), after step (2) but prior to step (3), after step (3) but prior to step (4), after step (4), or at the same time as step (4).

In some embodiments of the present application, where $R_1$ in the compound of formula 7 is H, the process for preparing the compound of formula I from the compound of formula 7 comprises the following steps: (1) linking amino group on a pyrazole ring of the compound of formula 7 with a protecting group; (2) converting carboxy group of the compound obtained from step (1) into amido group; (3) converting amido group of the compound obtained from step (2) into cyano group; and (4) removing the protective group of amino group on the pyrazole ring of the compound obtained from step (3).

In some methods for preparing a compound of formula I of the present application, the process for preparing the compound of formula I from the compound of formula 7 are optionally carried out by scheme 1, scheme 2, scheme 3, scheme 4 or scheme 5:

scheme 1, when $R_1$ is an amino-protecting group,

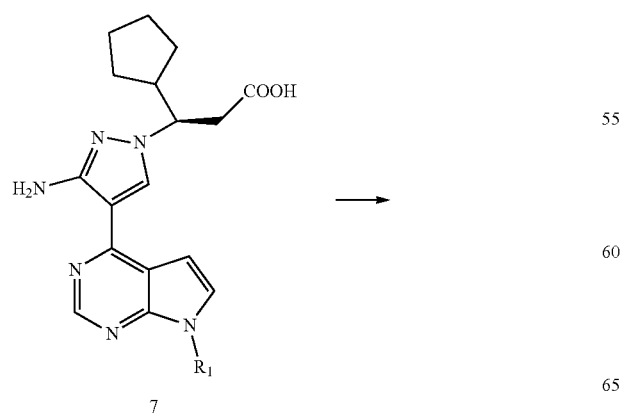

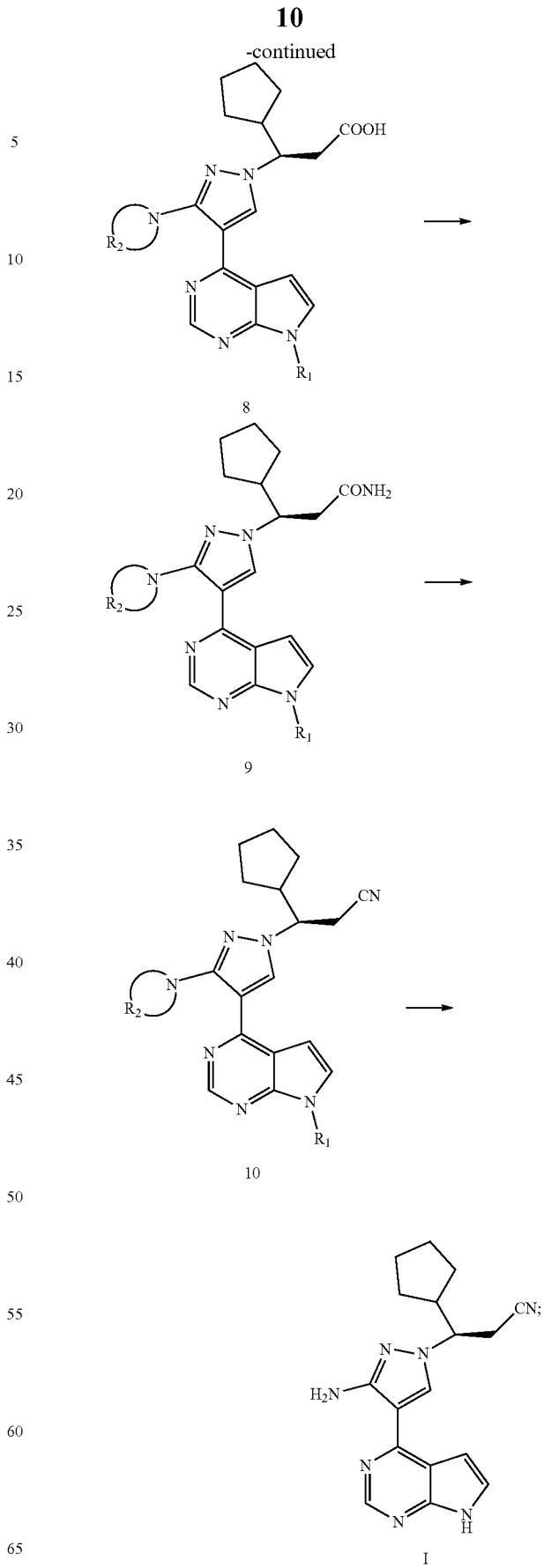

scheme 2, when R₁ is an amino-protecting group,
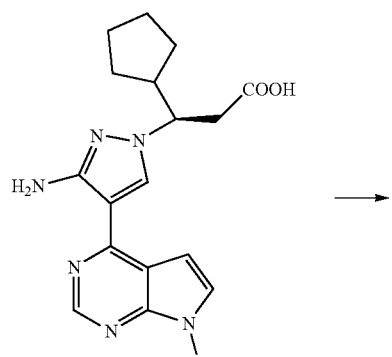
7
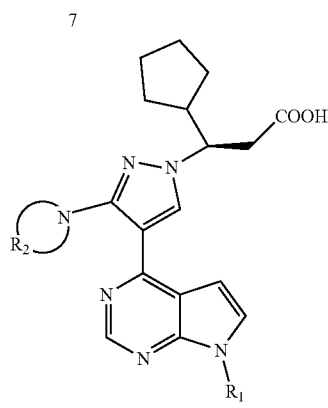
8
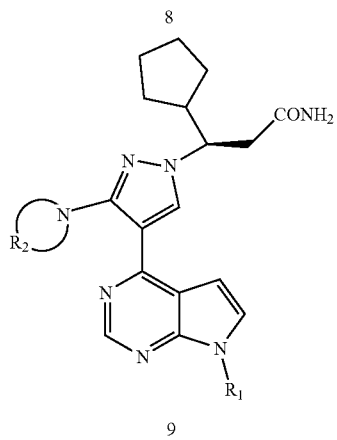
9
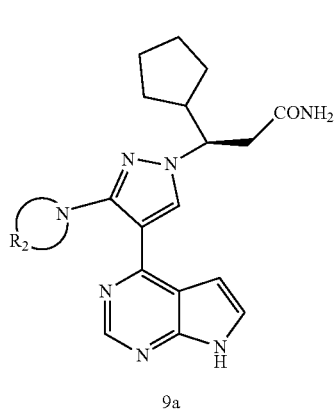
9a
-continued
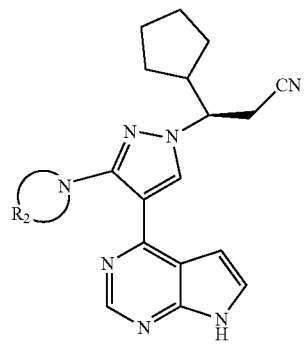
10a
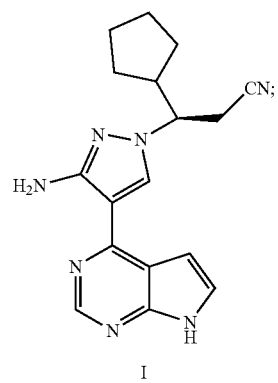
I
scheme 3, when R₁ is an amino-protecting group,
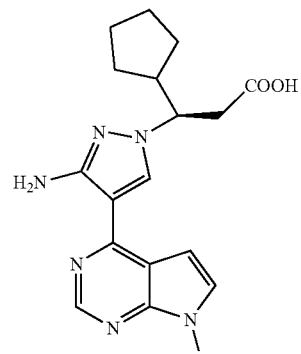
7
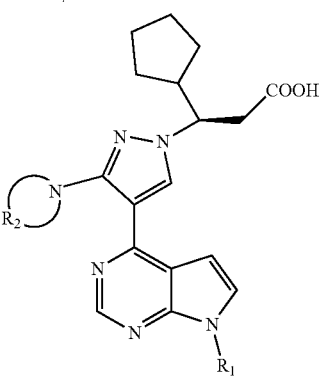
8

-continued
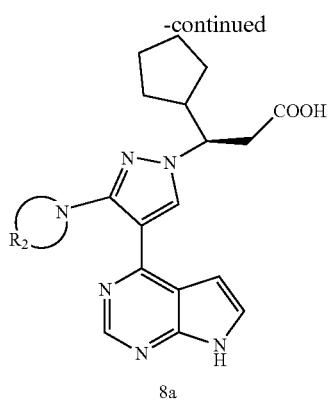
8a
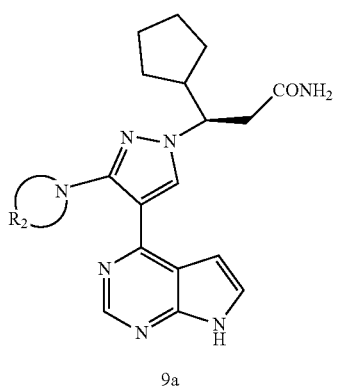
9a
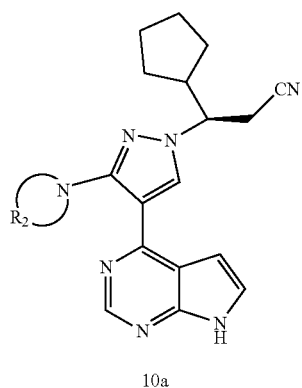
10a
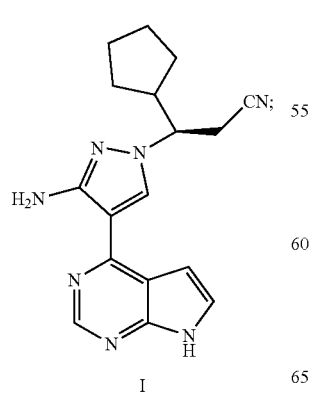
I
scheme 4, when R₁ is an amino-protecting group,
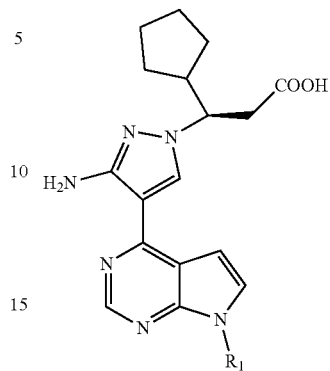
7
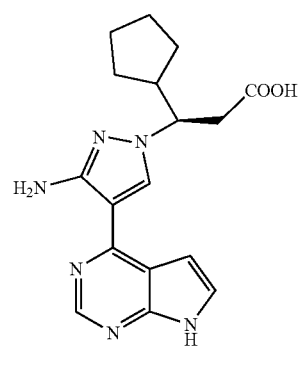
7b
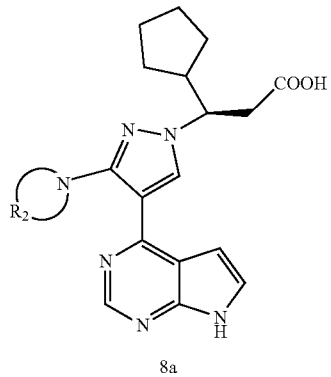
8a
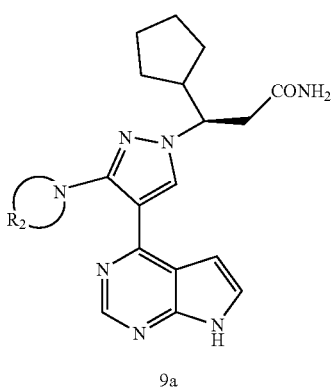
9a

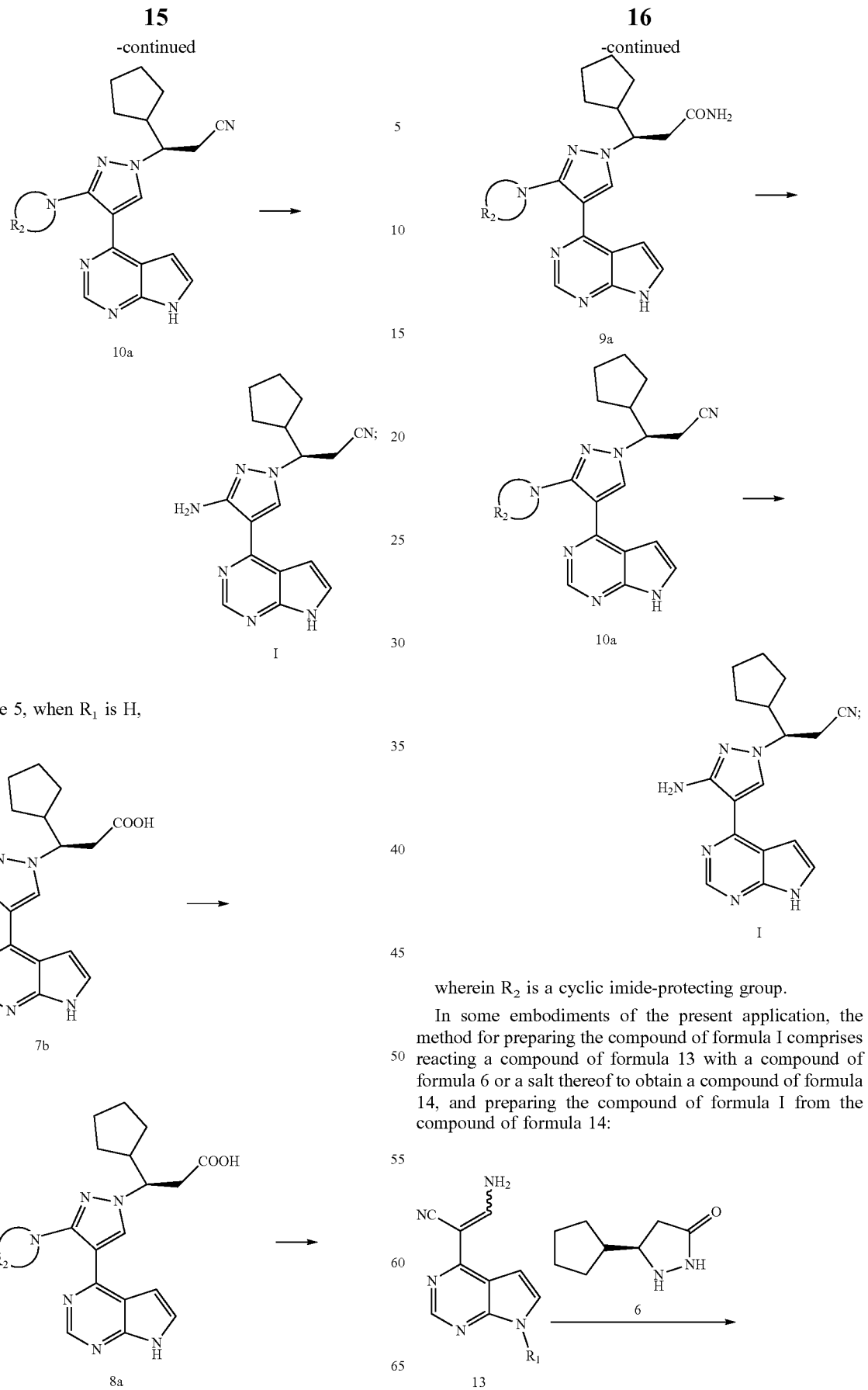
scheme 5, when $R_1$ is H,
wherein $R_2$ is a cyclic imide-protecting group.
In some embodiments of the present application, the method for preparing the compound of formula I comprises reacting a compound of formula 13 with a compound of formula 6 or a salt thereof to obtain a compound of formula 14, and preparing the compound of formula I from the compound of formula 14:

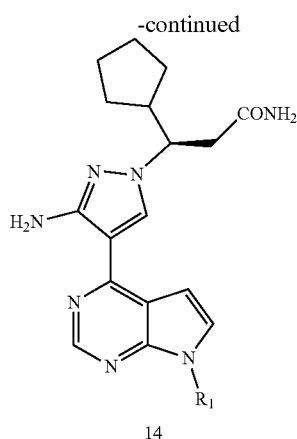

14

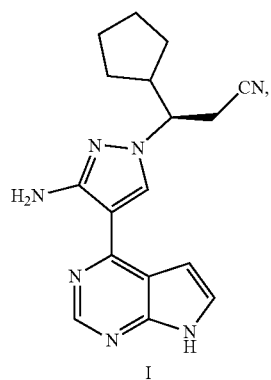

I wherein R$_1$ is selected from the group consisting of H and an amino-protecting group.

In some methods for preparing a compound of formula I of the present application, the process for preparing the compound of formula I from the compound of formula 14 optionally comprises: f) a reaction of converting amido group into cyano group, g) a reaction of linking amino group on a pyrazole ring with a protecting group, h) a reaction of removing the protective group of amino group on the pyrazole ring, and/or i) a reaction of removing R$_1$. The description manner of the aforementioned four reactions does not limit the occurrence order of these reactions. A person skilled in the art can change the occurrence order of the aforementioned four reactions according to the actual situation, or can combine two or more of the aforementioned reactions to occur simultaneously, both of which are within the protection scope of the present application.

In the process for preparing the compound of formula I from the compound of formula 14 of some methods for preparing a compound of formula I of the present application, optionally, the order of h) a reaction of removing the protective group of amino group on the pyrazole ring and i) a reaction of removing R$_1$ can be that h) a reaction of removing the protective group of amino group on the pyrazole ring occurs prior to i) a reaction of removing R$_1$, or i) a reaction of removing R$_1$ occurs prior to h) a reaction of removing the protective group of amino group on the pyrazole ring, or h) a reaction of removing the protective group of amino group on the pyrazole ring and i) a reaction of removing R$_1$ occur simultaneously.

In the process for preparing the compound of formula I from the compound of formula 14 of some methods for preparing a compound of formula I of the present application, optionally, g) a reaction of linking amino group on a pyrazole ring with a protecting group occurs prior to f) a reaction of converting amido group into cyano group, or g) a reaction of linking amino group on a pyrazole ring with a protecting group occurs prior to i) a reaction of removing R$_1$.

In some embodiments of the present application, when R$_1$ in the compound of formula 14 is an amino-protecting group, the process for preparing the compound of formula I from the compound of formula 14 comprises the following steps: (1) linking amino group on a pyrazole ring of the compound of formula 14 with a protecting group; (2) converting amido group of the compound obtained from step (1) into cyano group; (3) removing the protective group of amino group on the pyrazole ring of the compound obtained from step (2), and (4) removing R$_1$ prior to step (1), after step (1) but prior to step (2), after step (2) but prior to step (3), after step (3), or at the same time as step (3).

In some embodiments of the present application, when R$_1$ in the compound of formula 14 is H, the process for preparing the compound of formula I from the compound of formula 14 comprises the following steps: (1) linking amino group on a pyrazole ring of the compound of formula 14 with a protecting group; (2) converting amido group of the compound obtained from step (1) into cyano group; and (3) removing the protective group of amino group on the pyrazole ring of the compound obtained from step (2).

In the method for preparing a compound of formula I of the present application, the process for preparing the compound of formula I from the compound of formula 14 are optionally carried out by scheme 6, scheme 7, scheme 8, or scheme 9:

scheme 6, when R$_1$ is an amino-protecting group,

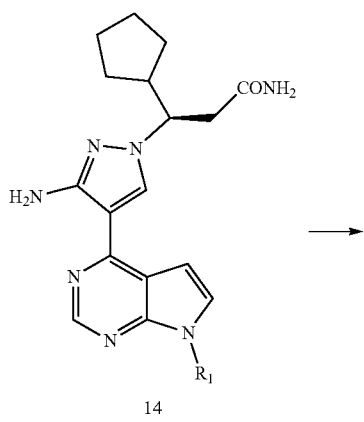

14

-continued
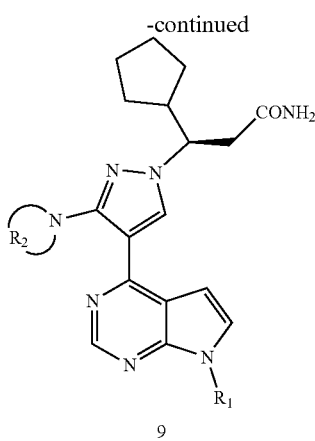
9
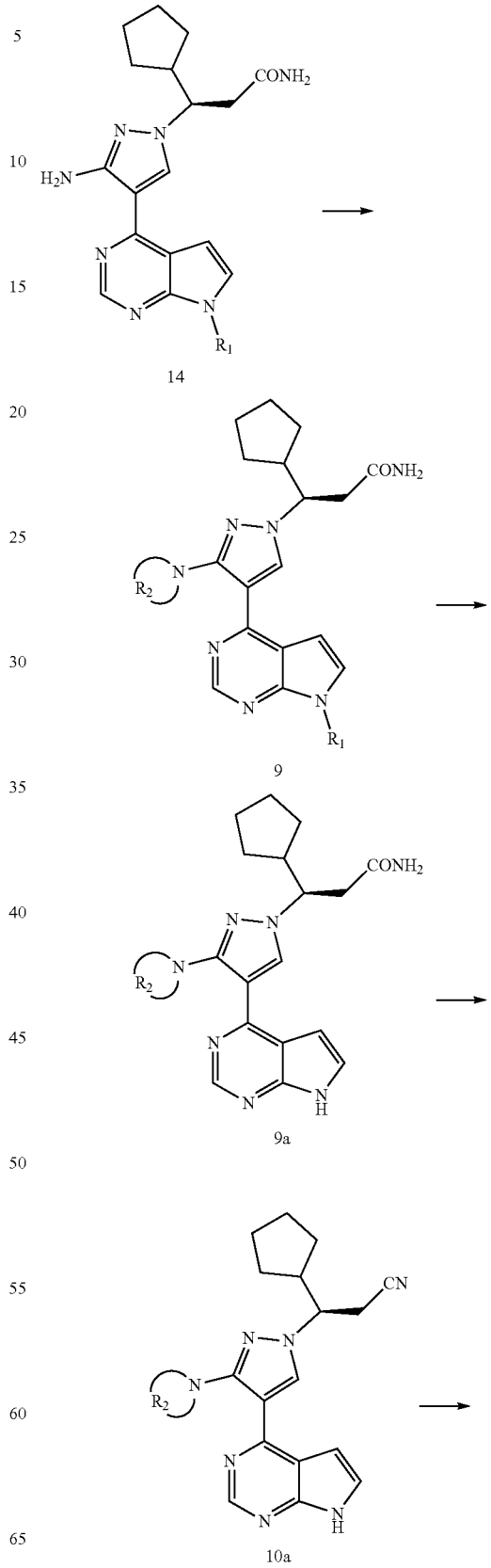
scheme 7, when $R_1$ is an amino-protecting group,

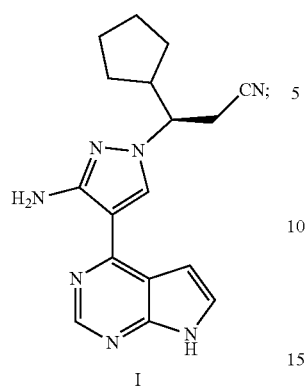
I
scheme 8, when $R_1$ is an amino-protecting group,
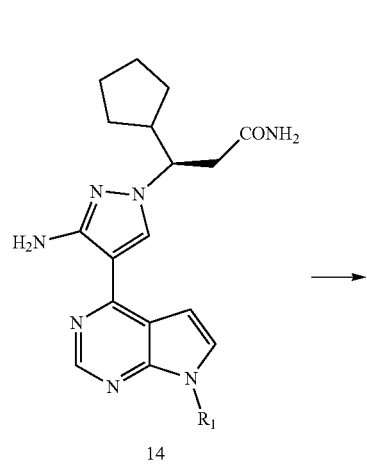
14
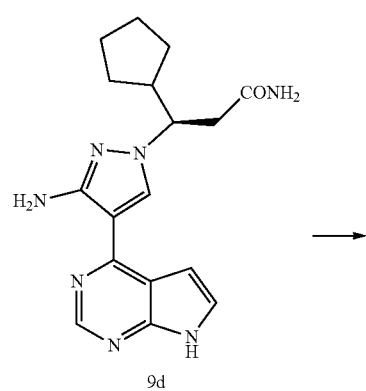
9d
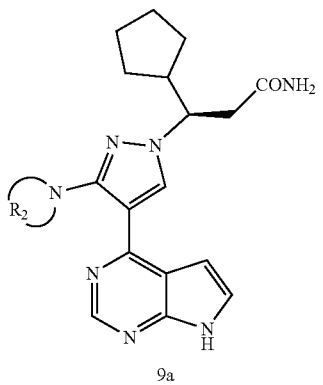
9a
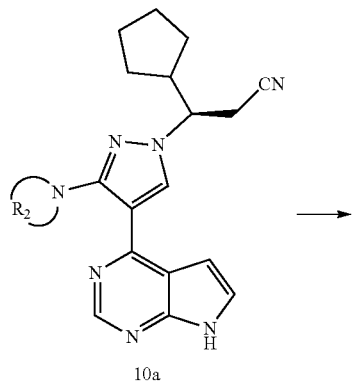
10a
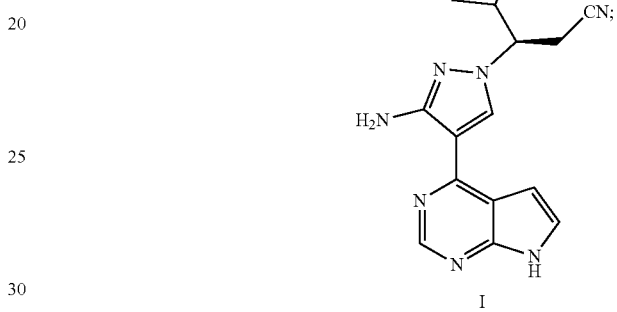
I
scheme 9, when $R_1$ is H,
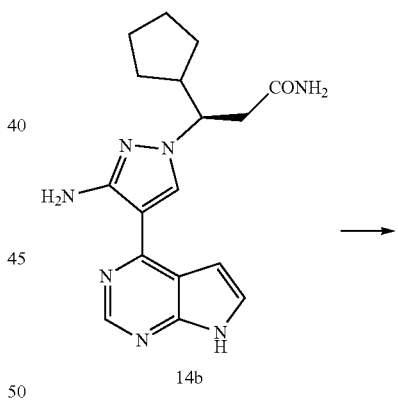
14b
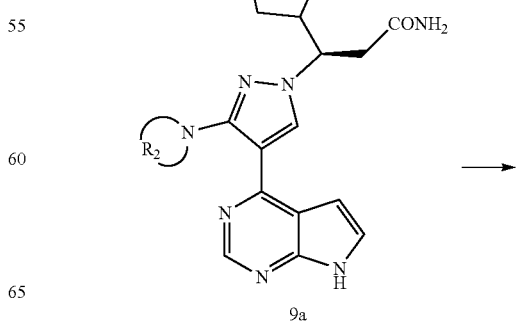
9a 23
-continued

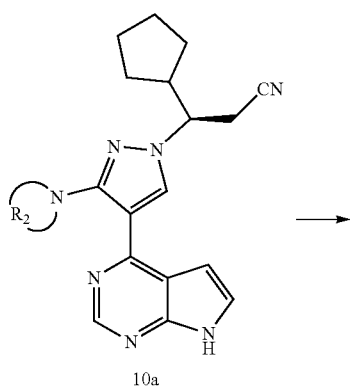

10a wherein R₂ is a cyclic imide-protecting group.

In another aspect, the present application provides a method for preparing a compound of formula 7, comprising reacting a compound of formula 5 with a compound of formula 6 or a salt thereof to obtain the compound of formula 7:

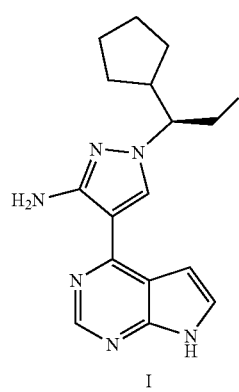

5

24
-continued

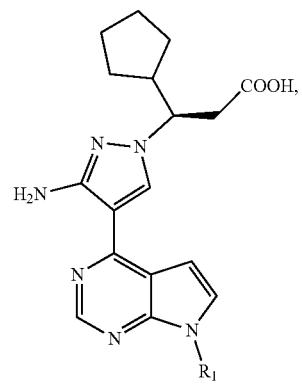

7 wherein R₁ is selected from the group consisting of H and an amino-protecting group.

In another aspect, the present application provides a method for preparing a compound of formula 14, comprising reacting a compound of formula 13 with a compound of formula 6 or a salt thereof to obtain the compound of formula 14:

14 wherein R₁ is selected from the group consisting of H and an amino-protecting group.

In another aspect, the present application provides a use of a reaction of a compound of formula 5 and a compound of formula 6 or a salt thereof to obtain a compound of formula 7 in the preparation of a compound of formula I:

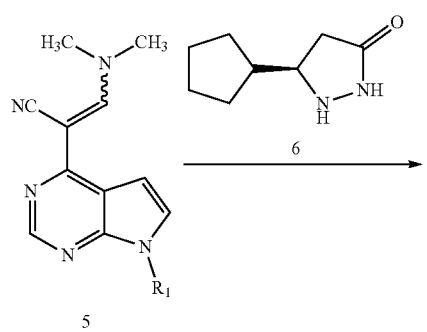
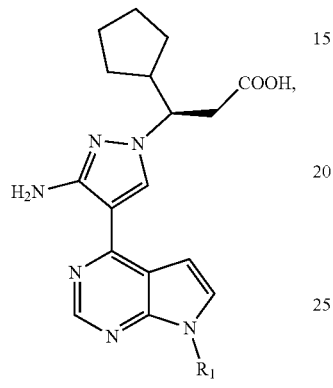
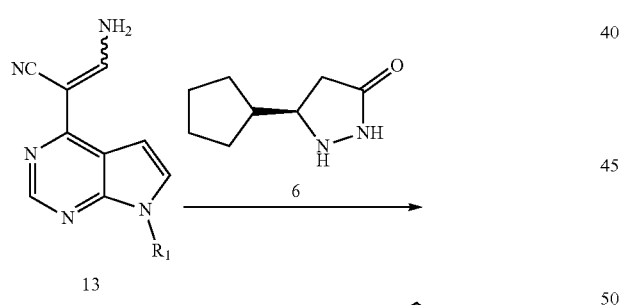
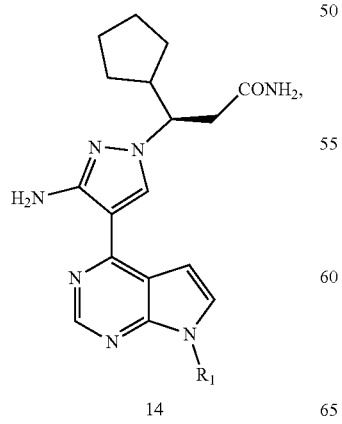

wherein R₁ is selected from the group consisting of H and an amino-protecting group.

In another aspect, the present application provides a use of a reaction of a compound of formula 13 and a compound of formula 6 or a salt thereof to obtain a compound of formula 14 in the preparation of a compound of formula I:

wherein R₁ is selected from the group consisting of H and an amino-protecting group.

In yet another aspect, the present application provides a compound of formula I, a compound of formula 12, and a compound of formula 13 as follows:

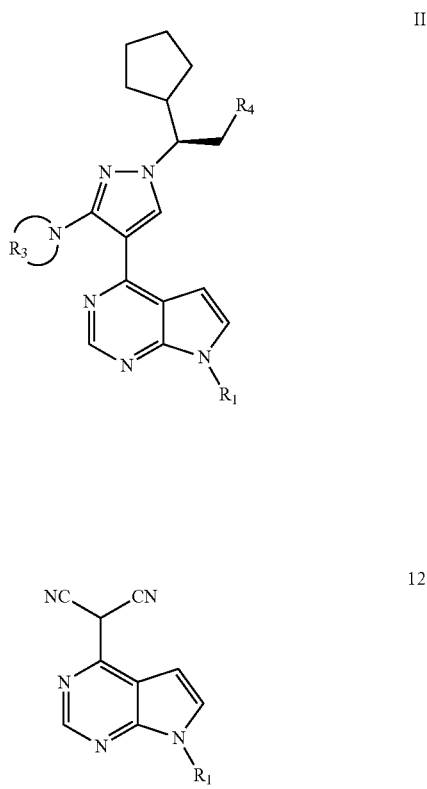
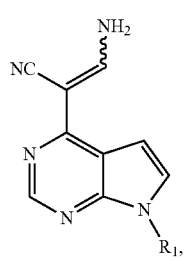

wherein R₁ is selected from the group consisting of H and an amino-protecting group; R₃ is selected from the group consisting of H and acyclic imide-protecting group; and R₄ is selected from the group consisting of —COOH, —CONH₂, and —CN, with the proviso that if R₄ is —CN, R₁ and R₃ are not both H.

In yet another aspect, the present application provides a use of compounds of formula II, formula 12, and formula 13 in the preparation of a compound of formula

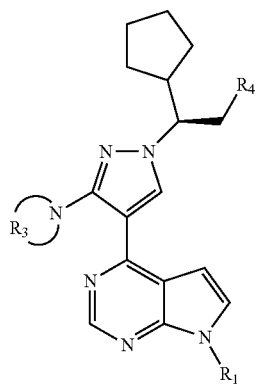

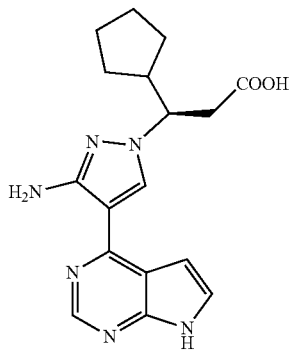

wherein R₁ is selected from the group consisting of H and an amino-protecting group; R₃ is selected from the group consisting of H and acyclic imide-protecting groups; and R₄ is selected from the group consisting of —COOH, —CONH₂, and —CN, with the proviso that if R₄ is —CN, R₁ and R₃ are not both H.

In some embodiments of the present application, the compound of formula II is selected from the group consisting of

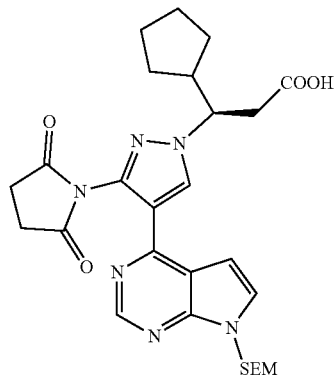

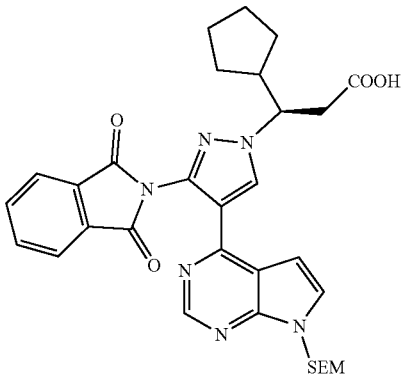

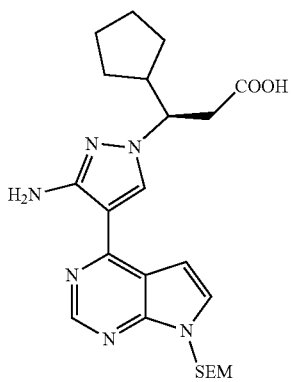

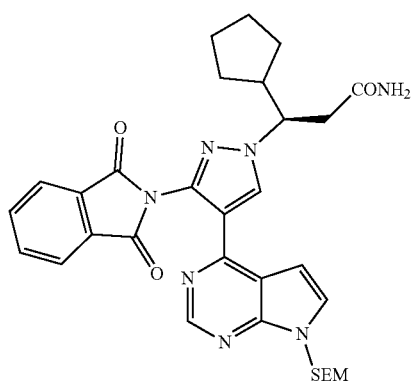 9c
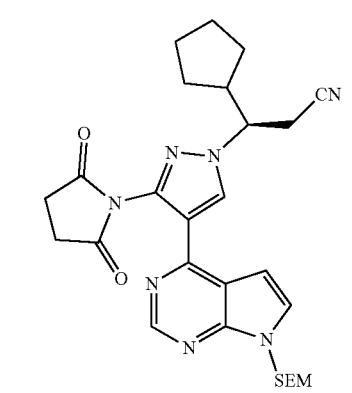 9d
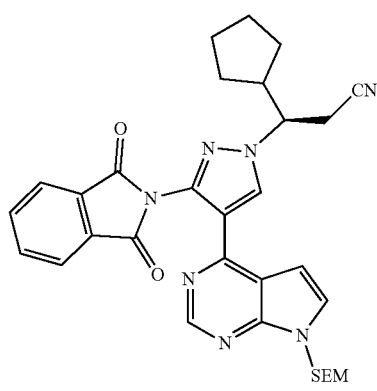 10b
10c
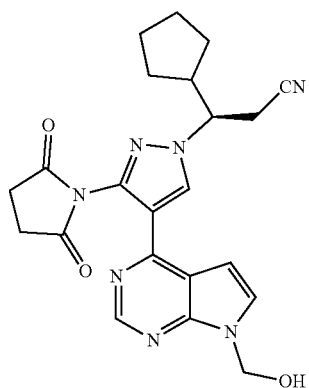 5
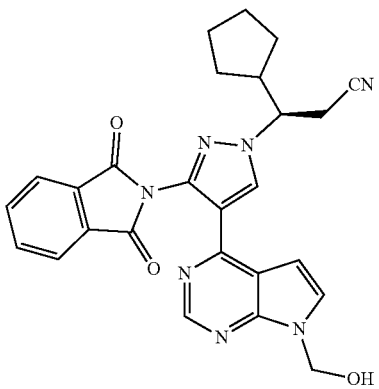 11a
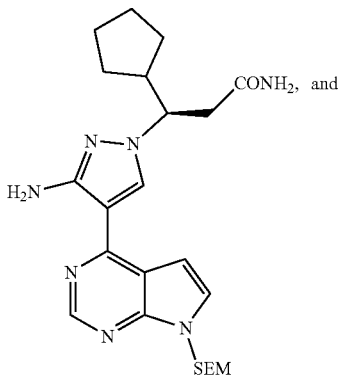 11b
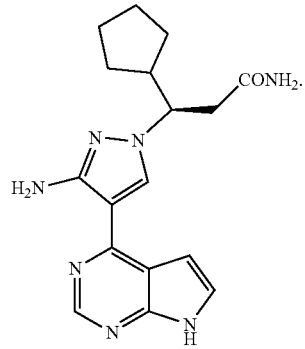 14a
14b In some embodiments of the present application, the compound of formula 12 is

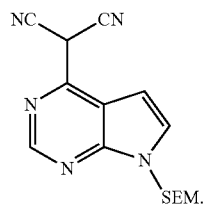

12a

In some embodiments of the present application, the compound of formula 13 is

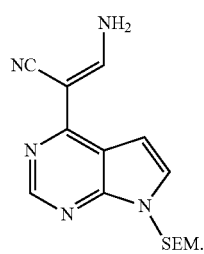

13a

In some embodiments of the present application, the amino-protecting groups is selected from the group consisting of hydroxymethyl, benzyloxycarbonyl (Cbz), 2,2,2-trichloroethoxycarbonyl (Troc), 2-(trimethylsilyl)ethoxycarbonyl (Teoc), 2-(4-trifluoromethylbenzenesulfonyl)ethoxycarbonyl (Tsc), tert-butyloxycarbonyl (Boc), 1-adamantyloxocarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBoc), vinyl, 2-chloroethyl, 2-benzenesulfonylethyl, p-nitrobenzenesulfonyl, p-methylbenzenesulfonyl, benzenesulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butyloxymethyl (Bum), benzyloxymethyl (Bom), 2-tetrahydropyranyl (THP), tri (C$_{1-4}$ alkyl)silyl, 1,1-diethoxymethyl, 2-(trimethylsilyl)ethoxymethyl (SEM), and N-pivaloyloxymethyl (POM), preferably hydroxymethyl, 2-(trimethylsilyl)ethoxymethyl (SEM), N-pivaloyloxymethyl (POM), p-nitrobenzenesulfonyl, p-methylbenzenesulfonyl, benzenesulfonyl, methanesulfonyl, and benzyl, and more preferably hydroxymethyl and 2-(trimethylsilyl)ethoxymethyl (SEM).

In some embodiments of the present application, the cyclic imide-protecting group is selected from the group consisting of

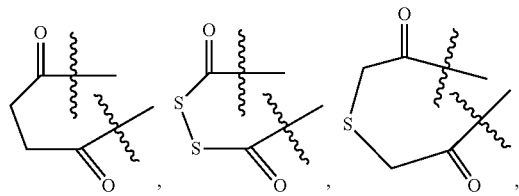

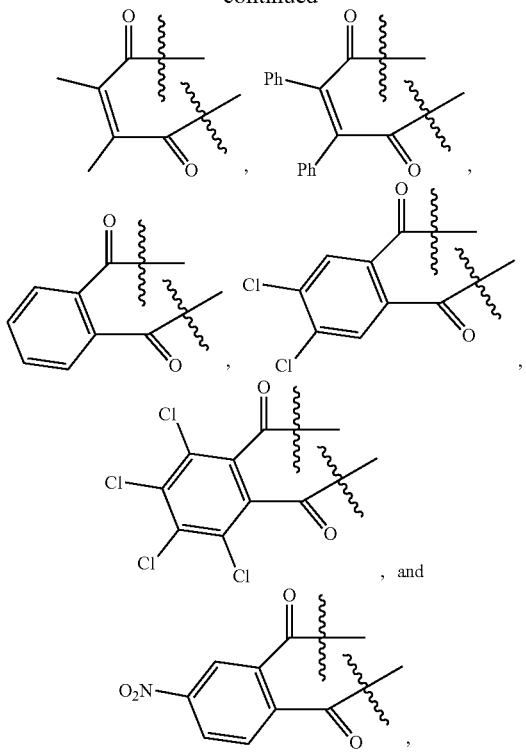

and preferably

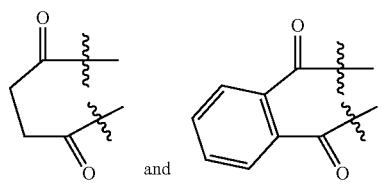

In some embodiments of the present application, a salt of the compound of formula 6 is selected from the group consisting of a chiral salt and an achiral salt.

In some embodiments of the present application, a chiral acid for forming a chiral salt of the compound of formula 6 is selected from the group consisting of mandelic acid, 2-chloromandelic acid, camphoric acid, lactic acid, malic acid, 3-bromocamphor-8-sulfonic acid, 3-bromocamphor-10-sulfonic acid, 10-camphorsulfonic acid, 2-amino-7,7-dimethyl-bicyclo[2,2,1]hept-1-ylidenesulfonic acid, 2-acrylamido-7,7-dimethyl-bicyclo[2,2,1]hept-1-ylidenesulfonic acid, or tartaric acid and its acyl derivative, or an enantiomer excess form thereof, preferably lactic acid, malic acid, camphoric acid, 10-camphorsulfonic acid, tartaric acid, diacetyltartaric acid, dibenzoyltartaric acid, di-p-methylbenzoyltartaric acid, di-p-methoxybenzoyltartaric acid, di-p-chlorobenzoyltartaric acid, di-p-bromobenzoyltartaric acid, di-p-fluorobenzoyl tartaric acid, di-p-nitrobenzoyltartaric acid, di-p-aminobenzoyltartaric acid, and di-p-cyanobenzoyltartaric acid, and more preferably tartaric acid, diacetyltartaric acid, dibenzoyltartaric acid, and di-p-methylbenzoyltartaric acid.

In some embodiments of the present application, a chiral acid for forming a chiral salt of the compound of formula 6 is selected from the group consisting of D-tartaric acid, D-diacetyltartaric acid, D-dibenzoyltartaric acid, D-di-p-methylbenzoyltartaric acid, D-di-p-methoxybenzoyltartaric acid, D-di-p-chlorobenzoyltartaric acid, D-di-p-bromobenzoyltartaric acid, D-di-p-fluorobenzoyltartaric acid, D-di-p-nitrobenzoyltartaric acid, D-di-p-aminobenzoyl tartaric acid, and D-di-p-cyanobenzoyltartaric acid.

In some embodiments of the present application, an achiral salt of the compound of formula 6 is selected from the group consisting of hydrochloride, hydrobromate, nitrate, sulfate, phosphate, formate, acetate, trifluoroacetate, fumarate, oxalate, maleate, citrate, succinate, mesylate, benzenesulfonate, and p-methylbenzenesulfonate, preferably hydrochloride, hydrobromate, sulfate, formate, acetate, trifluoroacetate, fumarate, maleate, mesylate, and p-methylbenzenesulfonate, and more preferably hydrochloride and acetate.

In some embodiments of the present application, a molar ratio of the compound of formula 5 to the compound of formula 6 is 1.0:1.0~5.0, preferably 1.0:1.0~3.0, more preferably 1.0:1.0~2.0, further preferably 1.0:1.0, 1.0:1.1, 1.0:1.2, 1.0:1.3, 1.0:1.4, 1.0:1.5, 1.0:1.6, 1.0:1.7, 1.0:1.8, 1.0:1.9, or 1.0:2.0, and further more preferably 1.0:1.2.

In some embodiments of the present application, the compound of formula 5 reacts with the compound of formula 6 or a salt thereof to obtain the compound of formula 7 under a neutral or basic condition. The basic condition is achieved by adding one or more of the following basic reagents: sodium hydroxide, potassium hydroxide, lithium hydroxide, potassium carbonate, cesium carbonate, sodium carbonate, potassium bicarbonate, sodium bicarbonate, sodium acetate, potassium acetate, sodium methoxide, potassium methoxide, sodium propionate, potassium propionate, sodium tert-butoxide, potassium tert-butoxide, triethylamine, diisopropylethylamine or DBU, preferably sodium acetate, potassium acetate, sodium methoxide, potassium methoxide, sodium propionate, potassium propionate, sodium tert-butoxide, or potassium tert-butoxide, and more preferably sodium acetate or potassium acetate. A molar ratio of the compound of formula 5 to the basic reagent is 1.0:1.0~5.0, preferably 1.0:1.0~3.0, more preferably 1.0:1.0~2.0, further preferably 1.0:1.0, 1.0:1.1, 1.0:1.2, 1.0:1.3, 1.0:1.4, 1.0:1.5, 1.0:1.6, 1.0:1.7, 1.0:1.8, 1.0:1.9, or 1.0:2.0, and further more preferably 1.0:1.5.

In some embodiments of the present application, the compound of formula 5 reacts with the compound of formula 6 or a salt thereof to obtain the compound of formula 7 in the presence of a solvent selected from the group consisting of toluene, xylene, DMSO, N-methylpyrrolidone, N,N-dimethylformamide, and N,N-dimethylacetamide, or a mixed solvent of two or more of the above solvents, and preferably N-methylpyrrolidone.

In some embodiments of the present application, the compound of formula 5 reacts with the compound of formula 6 or a salt thereof to obtain the compound of formula 7 at a reaction temperature of 80~180° C., and preferably 80° C., 90° C., 100° C., 110° C., 120° C., 130° C., 140° C., 150° C., 160° C., 170° C., or 180° C.

In some embodiments of the present application, a molar ratio of the compound of formula 13 to the compound of formula 6 is 1.0:1.0~5.0, preferably 1.0:1.0~3.0, more preferably 1.0:1.0~2.0, further preferably 1.0:1.0, 1.0:1.1, 1.0:1.2, 1.0:1.3, 1.0:1.4, 1.0:1.5, 1.0:1.6, 1.0:1.7, 1.0:1.8, 1.0:1.9, or 1.0:2.0, and further more preferably 1.0:1.2.

In some embodiments of the present application, the compound of formula 13 reacts with the compound of formula 6 or a salt thereof to obtain the compound of formula 14 under a neutral or basic condition. The basic condition is achieved by adding one or more of the following basic reagents: sodium hydroxide, potassium hydroxide, lithium hydroxide, potassium carbonate, cesium carbonate, sodium carbonate, potassium bicarbonate, sodium bicarbonate, sodium acetate, potassium acetate, sodium methoxide, potassium methoxide, sodium propionate, potassium propionate, sodium tert-butoxide, potassium tert-butoxide, triethylamine, diisopropylethylamine or DBU, preferably triethylamine, diisopropylethylamine or DBU, and more preferably diisopropylethylamine. The molar ratio of the compound of formula 13 to the basic reagent is 1.0:1.0~5.0, preferably 1.0:1.0~3.0, more preferably 1.0:1.0~2.0, further preferably 1.0:1.0, 1.0:1.1, 1.0:1.2, 1.0:1.3, 1.0:1.4, 1.0:1.5, 1.0:1.6, 1.0:1.7, 1.0:1.8, 1.0:1.9, or 1.0:2.0, and further more preferably 1.0:1.5.

In some embodiments of the present application, the compound of formula 13 reacts with the compound of formula 6 or a salt thereof to obtain the compound of formula 14 in the presence of a solvent selected from the group consisting of toluene, xylene, DMSO, N-methylpyrrolidone, N,N-dimethylformamide and N,N-dimethylacetamide, or a mixed solvent of two or more of the above solvents, and preferably N-methylpyrrolidone.

In some embodiments of the present application, the compound of formula 13 reacts with the compound of formula 6 or a salt thereof to obtain the compound of formula 14 at a reaction temperature of 80~180° C., and preferably 80° C., 90° C., 100° C., 110° C., 120° C., 130° C., 140° C., 150° C., 160° C., 170° C., or 180° C.

In some embodiments of the present application, the reaction of converting carboxy group into amido group (for example, the compound of formula 9 is prepared from the compound of formula 8) comprises the reaction of converting carboxy group into acyl chloride, and then the reaction of converting acyl chloride into amido group. The reaction of converting carboxy group into acyl chloride and the reaction of converting acyl chloride into amido group can be carried out step-by-step, and also can be carried out through a "one-pot method". A reagent used in the reaction of converting carboxy group into acyl chloride is selected from the group consisting of phosphorus trichloride, phosphorus pentachloride, thionyl chloride, oxalyl chloride, or a combination thereof, and preferably oxalyl chloride. A solvent used in the reaction of converting carboxy group into acyl chloride is selected from the group consisting of tetrahydrofuran, dichloromethane, trichloromethane, chlorobenzene, acetonitrile, DMA, NMP, ethyl acetate, isopropyl acetate, toluene and xylene, or a mixed solvent of two or more of the above solvents, and preferably NMP, tetrahydrofuran, dichloromethane, or a mixed solvent thereof. The reaction of converting acyl chloride into amido group is carried out in the presence of an amination reagent. The amination reagent is selected from the group consisting of aqueous ammonia, liquid ammonia, ammonia gas, and a combination thereof, and preferably aqueous ammonia and ammonia gas. The reaction of converting acyl chloride to amido group is carried out in the presence of a solvent selected from the group consisting of tetrahydrofuran, dichloromethane, trichloromethane, chlorobenzene, acetonitrile, DMA, NMP, ethyl acetate, isopropyl acetate, toluene, and xylene, or a mixed solvent of two or more of the above solvents, and preferably NMP, tetrahydrofuran, dichloromethane, or a mixed solvent thereof.

In some embodiments of the present application, the reaction of converting amido group to cyano group (for example, the compound of formula 10 is prepared from the compound of formula 9) is carried out in the presence of a dehydrating agent. The dehydrating agent is selected from the group consisting of phosphorus oxychloride, cyanuric chloride, phosphorus pentoxide, thionyl chloride, trifluoroacetic anhydride, trifluorosulfonic anhydride, oxalyl chloride, and a combination thereof, and preferably phosphorus oxychloride and cyanuric chloride. The reaction of converting amido group to cyano group is carried out in the presence of a solvent selected from the group consisting of tetrahydrofuran, dichloromethane, trichloromethane, chlorobenzene, acetonitrile, DMA, NMP, DMSO, ethyl acetate, isopropyl acetate, toluene, and xylene, or a mixed solvent of two or more of the above solvents, and preferably dichloromethane or NMP, or a mixed solvent thereof.

Description and Definition

In the present application, the term "SEM-" refers to 2-(trimethylsilyl)ethoxymethyl.

In the present application, when a chemical bond is represented by "⌇", it means that the direction of the chemical bond and an alkenyl group to which it is attached is not limited. For example, the compound of formula 5 includes the following structures:

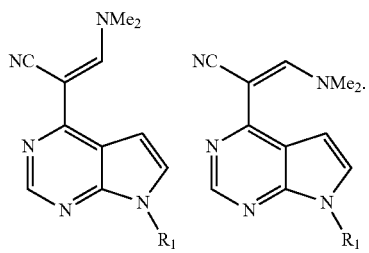

In the present application, where $R_3$ is H, the compound of formula II refers to the following structure:

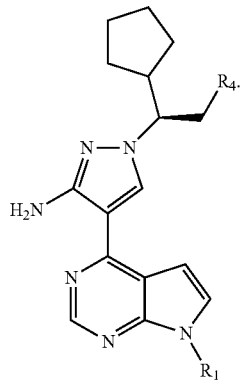

In the present application, the reaction of converting carboxy group into amido group refers to

In the present application, the reaction of converting amido group into cyano group refers to

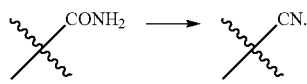

In the present application, the reaction of linking amino group on a pyrazole ring with a protecting group refers to

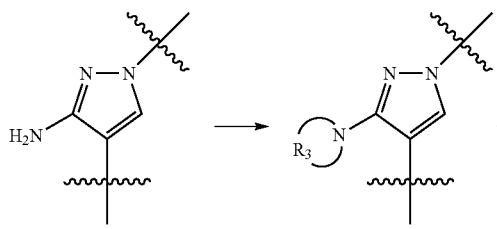

In the present application, the reaction of removing a protective group of amino group on a pyrazole ring refers to

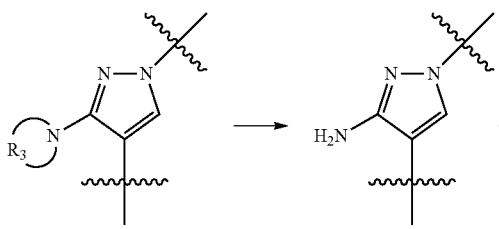

In the present application, the reaction of removing $R_1$ refers to

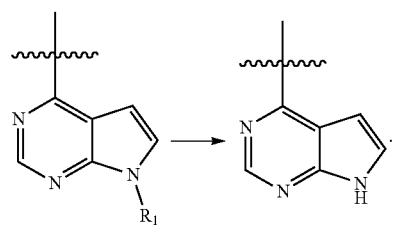

In the present application, the linking and removal of an amino-protecting group or acyclic imide-protecting group can be carried out through a conventional method in the art, and the method may be a one-step reaction, or a multi-step reaction, for example, but not limited to, those described in the "Greene's Protective Groups in Organic Synthesis, 4th Edition, Wiley Press" or the "Protecting Group Chemistry, Chemical Industry Press".

In some embodiments of the present application, the chiral compound is enantiomeric excess, and the enantiomeric excess refers to the content of a chiral isomer (the amount of a substance) equal to or greater than about 10%, about 20%, about 30%, about 40%, about 50%, about 60%, about 70%, about 80%, about 90%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 99.99%.

The graphical representations for racemic, ambiscalemic and scalemic, or enantiomerically pure compounds in the present application are obtained from Maehr, J. Chem. Ed. 1985, 62: 114-120. Unless specified otherwise, the wedge shaped bond and dotted line bond are used to represent the absolute configuration of a stereoscopic center. Where the compounds herein contain an olefinic double bond or other geometrically unsymmetrical center, unless specified otherwise, they comprise E-, Z-geometrical isomers. Similarly, the tautomer forms are all included within the scope of the present invention.

The compounds in the present application may have particular geometrical isomers or stereoisomer forms. Such compounds are all contemplated in the present application, including cis- and trans-isomers, (−)- and (+)-enantiomers, (R)- and (S)-enantiomers, diastereoisomers, (D)-isomers, (L)-isomers, and racemic mixtures thereof and other mixtures, such as a enantiomer or diastereoisomer-excess mixture. All such mixtures are included within the scope of the present application. Substituents such as alkyl group may have additional unsymmetrical carbon atoms. Such isomers and mixtures thereof are all included within the scope of the present invention.

In the present application, the reactions are optionally carried out in a solvent, and all of the solvents used in the present application are commercially available, and can be used without further purification. Reactions are usually carried out in an anhydrous solvent under an inert nitrogen gas atmosphere.

In the present application, proton nuclear magnetic resonance (NMR) data are recorded in BRUKER AVANCE III HD 500 M spectrometer with a chemical shift expressed in ppm in the low field of tetramethylsilane; and mass spectrometry was measured by Waters ACQUITY UPLC+ XEVO G2 QTof. The mass spectrometer is equipped with an electrospray ion source (ESI) operating in either positive or negative mode.

The preparation method of the present application has at least one of the following advantages: short steps, high stereoselectivity, high atom utilization, mild reaction conditions and simple post-treatment, avoids the use of an expensive asymmetric reaction catalyst, and is suitable for industrial production.

SPECIFIC EXAMPLES

The following examples further illustrate the technical solutions of the present invention describe in a detailed and non-limiting manner. They should not be considered as limiting the scope of the invention, but are merely illustration and typical representative of the present invention. The solvents, reagents and raw materials used in the present invention are commercially available chemically pure or analytically pure products.

Example 1: (3R)-3-{3-amino-4-{7H-pyrrolo[2,3-d]pyrimidin-4-yl}-1H-pyrazol-1-yl}-3-cyclopentylpropionitrile (I)

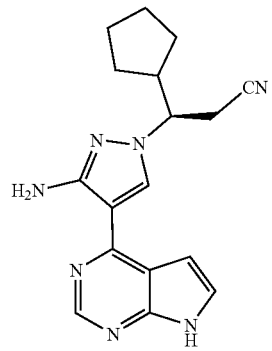

I

Step A: 3-cyclopentylacrylic acid

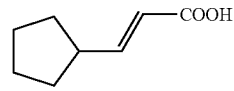

To a 5M solution of malonic acid (312 g, 3.0 mol, 1.0 eq.) in pyridine was added cyclopentanecarbaldehyde (344.4 g, 3.51 mol, 1.17 eq.) drop-wise at room temperature and stirred for 10 minutes; and then piperidine (6.2 g, 0.075 mol, 0.025 eq.) was slowly added drop-wise, and the reaction was stirred for additional 1 hour at room temperature. The reaction was warmed to 70~80° C. and stirred for 8 hours. The reaction mixture was concentrated under reduced pressure to evaporate the solvent, and the resulting residue was adjusted to pH 3.0 with the concentrated hydrochloric acid, and extracted with ethyl acetate three times. The organic phase was combined and washed with a 2.5M sodium hydroxide solution five times. The aqueous layer was adjusted to pH 3.0 with the concentrated hydrochloric acid and extracted with ethyl acetate three times. The organic layer was combined, washed with water three times, then washed with a saturated brine solution, dried over anhydrous sodium sulfate, filtrated and concentrated under reduced pressure to afford 3-cyclopentylacrylic acid (391.2 g, yield: 93%). $^1$H NMR (500 MHz, CDCl$_3$): δ 7.08 (dd, J=15.6, 8.1 Hz, 1H), 5.81 (dd, J=15.6, 1.1 Hz, 1H), 11.25 (s, 1H), 2.64 (m, 1H), 1.63 (m, 2H), 1.42 (m, 2H), 1.86 (m, 2H), 1.72 (m, 2H); HRMS (ESI) calcd. for C$_8$H$_{12}$O$_2$[M−H]$^-$ 139.0765; Found: 139.0760.

Step B: 5-cyclopentylpyrazolidin-3-one

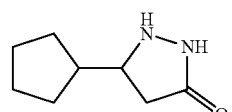

To cyclopentylacrylic acid (378 g, 2.7 mol, 1.0 eq.) was added 80% hydrazine hydrate (253.5 g, 4.05 mol, 1.5 eq.) drop-wise under stirring at room temperature and warmed to 70~80° C., and then the reaction was stirred for 6 hours. The reaction mixture was cooled to 0~10° C., stirred to precipitate crystals, and filtrated. The filter cake was washed with water twice, and forced air-dried for 12 hours at 45° C. to afford 5-cyclopentylpyrazolidin-3-one (292.5 g, yield: 68%).

Step C: R-5-cyclopentylpyrazolidin-3-one-D-tartrate

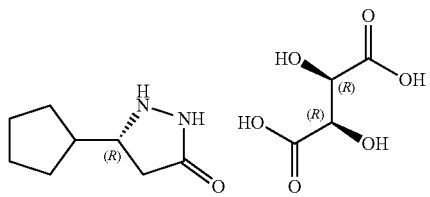

To a solution of 5-cyclopentylpyrazolidin-3-one (278 g, 1.8 mol, 1.0 eq.) in acetone was added D-tartaric acid (135 g, 0.9 mol, 0.5 eq.) under stirring at room temperature, and stirred for 2 hours to precipitate crystals, and then filtrated. The filter cake was slurried with acetone five times, and forced air-dried at 50° C. to afford R-5-cyclopentylpyrazolidin-3-one-D-tartrate (241 g, yield: 88%, ee value: 99.5%).

Step D: R-5-cyclopentylpyrazolidin-3-one (6)

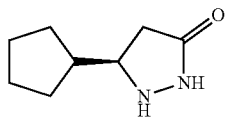

4M sodium hydroxide (52.2 g, 2.61 mol, 1.74 eq.) solution was added R-5-cyclopentylpyrazolidin-3-one-D-tartrate (228 g, 0.75 mol, 1.0 eq.) under stirring at room temperature, and was extracted with dichloromethane. The organic layer was combined, dried over anhydrous magnesium sulfate and filtrated, and the filtrate was concentrated under reduced pressure to afford R-5-cyclopentylpyrazolidin-3-one (6) (100.6 g, yield: 85.2%, 99.5% ee value). $^1$H-NMR (500 MHz, CDCl$_3$): δ 8.93 (s, 1H), 5.15 (s, 1H), 1.89 (m, 1H), 1.67 (m, 2H), 1.55 (m, 2H), 1.47 (m, 2H), 1.26 (m, 1H), 1.14 (m, 1H); HRMS (ESI) calcd. for C$_8$H$_{14}$N$_2$O [M+H]$^+$ 155.1179; Found: 155.1183.

Step E: 4-chloro-7-{[2-(trimethylsilyl)ethoxy]methyl}-7H-pyrrolo[2,3-d]pyrimidine (2)

To a solution of 4-chloropyrrolo[2,3-d]pyrimidine (200 g, 1.3 mol, 1.0 eq.) in N,N-dimethylformamide was added 60% NaH (62.4 g, 1.56 mol, 1.2 eq.) in an ice bath, and stirred for 1 hour at room temperature after completion of addition. 2-(Trimethylsilyl)ethoxymethyl chloride (SEMCl, 260 g, 1.56 mol, 1.2 eq.) was slowly added drop-wise under cooling in an ice bath. After completion of addition, the reaction was stirred for 1 hour in an ice bath, quenched with water, and extracted with ethyl acetate. The combined organic phase was washed with a saturated brine solution, dried over anhydrous sodium sulfate, and filtrated. The filtrate was concentrated under reduced pressure to obtain residue, which was purified by column chromatography on silica gel to afford 4-chloro-7-{[2-(trimethylsilyl)ethoxy]methyl}-7H-pyrrolo[2,3-d]pyrimidine (2) (312.2 g, yield: 91.8%). $^1$H-NMR (500 MHz, CDCl$_3$): δ 8.64 (s, 1H), 7.38 (d, J=3.6 Hz, 1H), 6.65 (d, J=3.6 Hz, 1H), 5.64 (s, 2H), 3.52 (t, J=8.2 Hz, 2H), 0.90 (t, J=8.2 Hz, 2H), −0.07 (s, 9H); HRMS (ESI) calcd. for C$_{12}$H$_{18}$N$_3$OSi [M+H]$^+$ 284.0980; Found: 284.0995.

Step F: Ethyl 2-cyano-2-{7-{[2-(trimethylsilyl)ethoxy]methyl}-7H-pyrrolo [2,3-d]pyrimidin-4-yl}acetate (3)

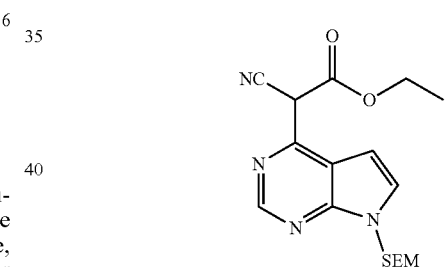

To a solution of 4-chloro-7-{[2-(trimethylsilyl)ethoxy]methyl}-7H-pyrrolo[2,3-d]pyrimidine (2) (142 g, 0.5 mol, 1.0 eq.) and ethyl cyanoacetate (85 g, 0.75 mol, 1.5 eq.) in DMF was added potassium carbonate (207 g, 1.5 mol, 3.0 eq.) under stirring at room temperature, and then heated to 120° C. and stirred for 4 hours at that temperature. The reaction was cooled to room temperature, quenched with water; stirred to precipitate crystals, and filtrated. The filter cake was washed with water, and forced air-dried at 50° C. to afford ethyl 2-cyano-2-{7-{[2-(trimethylsilyl)ethoxy]methyl}-7H-pyrrolo[2,3-d]pyrimidin-4-yl}acetate (3) (167 g, yield: 92.6%). $^1$H-NMR (500 MHz, CDCl$_3$): δ 13.46 (s, 1H), 8.45 (s, 1H), 7.56 (d, J=3.6 Hz, 1H), 7.18 (d, J=3.6 Hz, 1H), 5.56 (s, 2H), 4.32 (q, J=7.1 Hz, 2H), 3.52 (t, J=8.2 Hz, 2H), 1.27 (t, J=7.1 Hz, 3H), 0.83 (t, J=8.2 Hz, 2H), −0.08 (s, 9H); HRMS (ESI) calcd. for C$_{17}$H$_{24}$N$_4$O$_3$Si [M+H]$^+$ 361.1690; Found: 361.1699.

Step G: 2-{7-{[2-(trimethylsilyl)ethoxy]methyl}-7H-pyrrolo[2,3-d]pyrimidin-4-yl}acetonitrile (4)

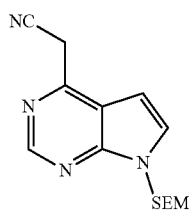

4

To a solution of ethyl 2-cyano-2-{7-{[2-(trimethylsilyl)ethoxy]methyl}-7H-pyrrolo[2,3-d]pyrimidin-4-yl}acetate (3) (162.2 g, 0.45 mol, 1.0 eq.) in a mixture of N-methylpyrrolidone and water was added sodium chloride (263 g, 4.5 mol, 10 eq.) under stirring at room temperature, and then heated to 160~170° C. and stirred for 30 hours. The reaction was quenched with water, and extracted with ethyl acetate, and the organic layer was washed with a saturated brine solution, filtrated over anhydrous sodium sulfate, filtrated and concentrated to obtain the residue, which was purified by column chromatography on silica gel to afford 2-{7-{[2-(trimethylsilyl)ethoxy]methyl}-7H-pyrrolo[2,3-d]pyrimidin-4-yl}acetonitrile (4) (98.6 g, yield: 76%). $^1$H-NMR (500 MHz, CDCl$_3$): δ 8.18 (s, 1H), 7.77 (d, J=3.4 Hz, 1H), 6.83 (d, J=3.4 Hz, 1H), 5.65 (s, 2H), 4.56 (s, 2H), 3.52 (t, J=7.6 Hz, 2H), 0.82 (t, J=7.6 Hz, 2H), −0.10 (s, 9H); HRMS (ESI) calcd. for C$_{14}$H$_{20}$N$_4$OSi [M+H]$^+$ 289.1479; Found: 289.1498.

Step H: 3-(dimethylamino)-2-{7-{[2-(trimethylsilyl)ethoxy]methyl}-7H-pyrrolo[2,3-d]pyrimidin-4-yl}acrylonitrile (5a)

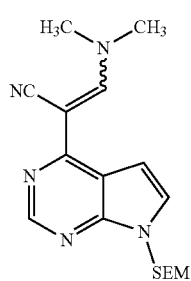

5a

To a solution of 2-{7-{[2-(trimethylsilyl)ethoxy]methyl}-7H-pyrrolo[2,3-d]pyrimidin-4-yl}acetonitrile (4) (95 g, 0.33 mol, 1.0 eq.) in DMF was added DMF-DMA (119 g, 1.0 mol, 3.0 eq.), and warmed to reflux for 2 hours. Then the reaction was cooled to room temperature, stirred to precipitate crystals after the addition of water, and then filtrated. The filter cake was washed with water, and forced air-dried at 50° C. to afford 3-(dimethylamino)-2-{7-{[2-(trimethylsilyl)ethoxy]methyl}-7H-pyrrolo[2,3-d]pyrimidin-4-yl}acrylonitrile (5a) (106.5 g, yield: 94%). $^1$H-NMR (500 MHz, CDCl$_3$): M 8.50 (s, 1H), 8.38 (s, 1H), 7.26 (d, J=3.7 Hz, 1H), 7.18 (d, J=3.7 Hz, 1H), 5.56 (s, 2H), 3.49 (t, J=8.4 Hz, 2H), 3.43 (s, 3H), 3.23 (s, 3H), 0.87 (t, J=8.4 Hz, 2H), −0.10 (s, 9H); HRMS (ESI) calcd. for C$_{17}$H$_{25}$N$_5$OSi [M+H]$^+$ 344.1901; Found: 344.1907.

Step I: (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentylpropionic acid (7a)

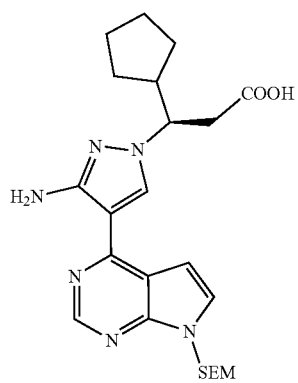

7a

To a solution of 3-(dimethylamino)-2-{7-{[2-(trimethylsilyl)ethoxy]methyl}-7H-pyrrolo[2,3-d]pyrimidin-4-yl}acrylonitrile (5a) (68.7 g, 0.2 mol, 1.0 eq.) and R-5-cyclopentylpyrazolidin-3-one (6) (37.0 g, 0.24 mol, 1.2 eq.) in N-methylpyrrolidone was added potassium acetate (1.5 eq.) under stirring at room temperature, and then heated to 120~130° C. and stirred for 12 hours. The reaction was quenched with water, and extracted with ethyl acetate. The organic layer was washed with water three times and then with a saturated brine solution, dried over anhydrous sodium sulfate, and filtrated. The filtrate was concentrated under reduced pressure to obtain the residue, which was purified by column chromatography on silica-gel to afford (R)-3-{3-amino-4{-7-{[2-(trimethylsilyl)ethoxy]methyl}-7H-pyrrolo[2,3-d]pyrimidin-4-yl}-1H-pyrazol-1-yl}-3-cyclopentylpropionic acid (7a) (37.6 g, yield: 40.1%, ee value: 99.8%). $^1$H-NMR (500 MHz, CDCl$_3$): δ 8.74 (s, 1H), 7.96 (s, 1H), 7.32 (d, J=3.4 Hz, 1H), 6.67 (d, J=3.4 Hz, 1H), 5.63 (m, 2H), 4.19 (t, J=8.2 Hz, 2H), 3.52 (m, 1H), 3.52 (t, J=8.4 Hz, 2H), 3.09 (dd, J=16.7, 8.2 Hz, 1H), 2.87 (d, J=16.7 Hz, 1H), 2.41 (m, 1H), 1.87 (m, 1H), 1.69 (m, 1H), 1.60 (m, 2H), 1.51 (m, 2H), 1.15 (m, 1H), 0.91 (t, J=8.4 Hz, 2H), −0.06 (s, 9H); FIRMS (ESI) calcd. for $C_{17}H_{25}N_5OSi$ [M+H]$^+$ 471.2534; Found: 471.2538.

Step J: (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentylpropionic acid (8b)

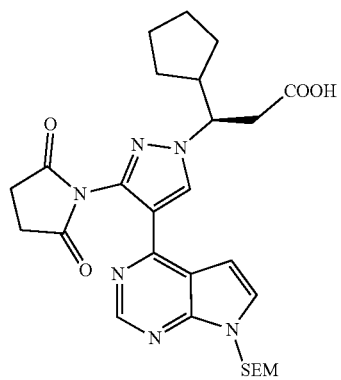

8b

To a 0.2 M solution of (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentylpropionic acid (7a) (35.0 g, 74.3 mmol, 1.0 eq.) in toluene was added butanedioic anhydride (10.4 g, 104 mmol, 1.4 eq.) under stirring at room temperature, and heated to reflux (water separation) for 14 hours under the protection of nitrogen gas. The reaction mixture was concentrated under reduced pressure to evaporate the solvent, and the residue was dissolved in ethyl acetate, and washed sequentially with water, a saturated sodium bicarbonate solution and a saturated brine solution. To ethyl acetate layer were added anhydrous sodium sulfate and activated carbon, stirred, dried, and decolored, and then filtrated and concentrated under reduced to afford (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentylpropionic acid (8b) (39 g, 70.6 mmol, yield: 40.1%). $^1$H-NMR (500 MHz, CDCl$_3$): δ 8.65 (s, 1H), 8.28 (s, 1H), 7.28 (d, J=3.7 Hz, 1H), 6.62 (d, J=3.7 Hz, 1H), 5.59 (d, J=11.1 Hz, 1H), 5.53 (d, J=11.1 Hz, 1H), 4.44 (td, J=9.9, 3.2 Hz, 1H), 3.48 (m, 2H), 3.02 (dd, J=16.8, 10.0 Hz, 1H), 2.83 (m, 1H), 2.43 (m, 1H), 1.78 (m, 1H), 1.69 (m, 1H), 1.61 (m, 1H), 1.52 (m, 1H), 1.51 (m, 1H), 1.50 (m, 2H), 1.14 (m, 1H), 0.88 (m, 2H), −0.07 (s, 9H); HRMS (ESI) calcd. for $C_{27}H_{36}N_6O_5Si$ [M+H]$^+$ 553.2589; Found: 553.2603.

Step K: (R)-3-cyclopentyl-3-[3-(2,5-dioxopyrrol-1-yl)-4-(7-{[2-(trimethylsilyl)ethoxy]methyl}-7H-pyrrolo[2,3-d]pyrimidin-4-yl)-1H-pyrazol-1-yl}propanamide (9b)

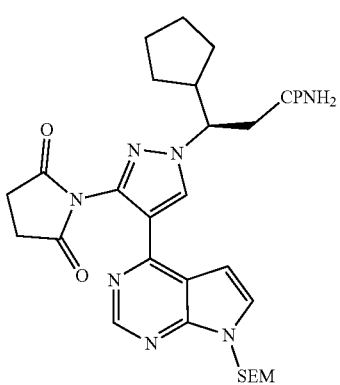

9b

To a 0.18M solution of (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentylpropionic acid (8b) (35.0 g, 63.3 mmol, 1.0 eq.) in dichloromethane was add oxalyl chloride (20.0 g, 158 mmol, 2.5 eq.) dropwise in an ice bath under stirring and the protection of nitrogen gas. After completion of addition, DMF (0.1 g, 1.3 mol, 0.02 eq.) was added drop-wise, and stirred for 1 h at room temperature. The reaction mixture was concentrated under reduced pressure to evaporate the solvent, and the residue was dissolved in THF which had been dried with sodium wire and redistilled, added to a 2M solution of aqueous ammonia (20.0, 0.32 mol, 5.0 eq.) in THF dropwise, and stirred for 30 min in an ice bath. The reaction mixture was concentrated under reduced pressure to evaporate THF, then cooled in an ice bath to precipitate crystals for 2 h, and filtrated. The filter cake was washed with water, and forced air-dried at 50° C. to afford (R)-3-cyclopentyl-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}propanamide (9b) (29.8 g, yield: 85.5%).

$^1$H-NMR (500 MHz, CDCl$_3$): δ 8.65 (s, 1H), 8.24 (s, 1H), 7.32 (d, J=3.7 Hz, 1H), 6.63 (d, J=3.7 Hz, 1H), 6.12 (s, 1H), 5.60 (d, J=11.1 Hz, 1H), 5.56 (d, J=11.1 Hz, 1H), 5.44 (s, 1H), 4.40 (td, J=10.6, 3.2 Hz, 1H), 3.47 (dd, J=9.1, 7.5 Hz, 2H), 2.99 (dd, J=14.4, 11.0 Hz, 1H), 2.91 (s, 4H), 2.67 (dd, J=14.4, 3.3 Hz, 1H), 2.48 (m, 1H), 1.84 (m, 1H), 1.66 (m, 1H), 1.58 (m, 2H), 1.57 (m, 1H), 1.50 (m, 1H), 1.31 (m, 1H), 1.21 (m, 1H), 0.88 (dd, 9.1, 7.5, 2H), −0.08 (s, 9H); FIRMS (ES) calcd. for $C_{27}H_{37}N_7O_4Si$ [M+H]$^+$ 552.2749; Found: 552.2759.

Step L: (R)-3-cyclopentyl-3-[3-(2,5-dioxopyrrol-1-yl)-4-(7-{[2-(trimethylsilyl) ethoxy]methyl}-7H-pyrrolo[2,3-d]pyrimidin-4-yl)-1H-pyrazol-1-yl}propionitrile (10b)

Step M: (R)-3-cyclopentyl-3-{3-(2,5-dioxopyrrol-1-yl)-4-{(7-hydroxymethyl)-7H-pyrrolo[2,3-d]pyrimidin-4-yl)-1H-pyrazol-1-yl}propionitrile (11a)

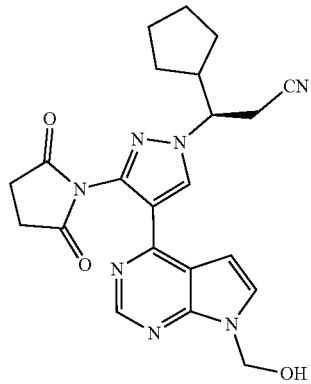

11a

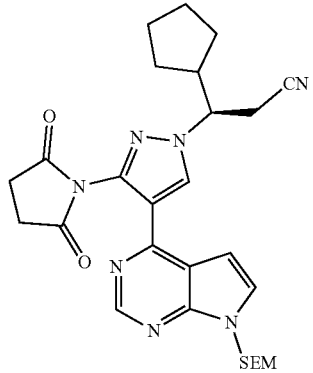

10b

To a 0.2M solution of (R)-3-cyclopentyl-3-[3-(2,5-dioxopyrrol-1-yl)-4-(7-{[2-(trimethylsilyl)ethoxy]methyl}-7H-pyrrolo[2,3-d]pyrimidin-4-yl)-1H-pyrazol-1-yl}propionitrile (10b) (20 g, 37.5 mmol, 1.0 eq.) in dichloromethane was added 47% boron trifluoride solution in diethyl ether drop-wise in an ice bath under stirring, and stirred for 4 hours at room temperature. The reaction was quenched with water, adjusted to pH6~7 with 10% NaOH solution, and extracted with ethyl acetate. The organic layer was washed sequentially with water and a saturated brine solution, dried over anhydrous magnesium sulfate, and filtered. The filtrate was concentrated under reduced pressure to afford (R)-3-cyclopentyl-3-[3-(2,5-dioxopyrrol-1-yl)-4-(7-hydroxymethyl)-7H-pyrrolo[2,3-d]pyrimidin-4-yl)-1H-pyrazol-1-yl]propionitrile (11a) (14.4 g, yield: 88.5%).

$^1$H-NMR (500 MHz, CDCl$_3$): δ 8.54 (s, 1H), 8.31 (s, 1H), 7.31 (d, J=3.7 Hz, 1H), 6.52 (d, J=3.7 Hz, 1H), 5.68 (d, J=10.9 Hz, 1H), 5.61 (d, J=10.9 Hz, 1H), 4.32 (m, 1H), 3.13 (dd, J=17.2, 7.9 Hz, 1H), 3.03 (dd, J=17.2, 4.3 Hz, 1H), 2.94 (s, 4H), 2.62 (m, 1H), 1.98 (m, 1H), 1.74 (m, 1H), 1.65 (m, 1H), 1.64 (m, 2H), 1.30 (m, 1H), 1.29 (m, 2H); HRMS (ESI) calcd. for C$_{22}$H$_{23}$N$_7$O$_3$ [M+H]$^+$ 434.1935; Found: 434.1944.

To a 0.2M solution of (R)-3-cyclopentyl-3-[3-(2,5-dioxopyrrol-1-yl)-4-(7-{[2-(trimethylsilyl)ethoxy]methyl}-7H-pyrrolo[2,3-d]pyrimidin-4-yl)-1H-pyrazol-1-yl}propanamide (9b) (25 g, 45.3 mmol, 1.0 eq.) in dichloromethane was added phosphorus oxychloride (27.8 g, 81 mmol, 4.0 eq.) drop-wise in an ice bath under stirring and stirred for 2 hours at room temperature after completion of addition. The reaction was quenched with water, and the organic layer was washed with water, stirred after the addition of anhydrous magnesium sulfate and activated carbon, dried, decolored, and then filtrated. The filtrated was concentrated under reduced pressure to remove the solvent to afford (R)-3-cyclopentyl-3-[3-(2,5-dioxopyrrol-1-yl)-4-(7-{[2-(trimethylsilyl)ethoxy]methyl}-7H-pyrrolo[2,3-d]pyrimidin-4-yl)-1H-pyrazol-1-yl}propionitrile (10b) (22.2 g, 41.7 mmol, yield: 92%).

Step N: (R)-3-amino-4-(7H-pyrrolo[2,3-d]pyrimidin-4-yl)-1H-pyrazol-1-yl}-3-cyclopentyl propionitrile (I)

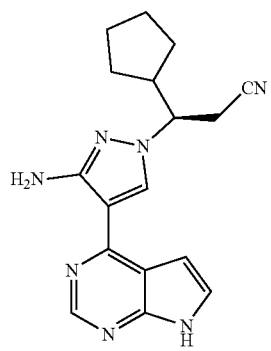

I $^1$H-NMR (500 MHz, CDCl$_3$): δ 8.70 (s, 1H), 8.35 (s, 1H), 7.35 (d, J=3.7 Hz, 1H), 6.66 (d, J=3.7 Hz, 1H), 5.62 (d, J=10.8 Hz, 1H), 5.58 (d, J=10.8 Hz, 1H), 4.30 (m, 1H), 3.50 (m, 2H), 3.09 (dd, J=16.8, 4.3 Hz, 1H), 3.01 (dd, J=16.8, 4.3 Hz, 1H), 2.94 (s, 4H), 2.62 (m, 1H), 1.96 (m, 1H), 1.69 (m, 2H), 1.60 (m, 1H), 1.58 (m, 2H), 1.27 (m, 2H), 0.90 (t, J=8.3 Hz, 2H), −0.06 (s, 9H); HRMS (ESI) calcd. for C$_{27}$H$_{35}$N$_7$O$_3$Si [M+H]$^+$ 534.2643; Found: 534.2657.

To a 0.2M solution of (R)-3-{3-(2,5-dioxopyrrol-1-yl)-4-(7-hydroxymethyl)-7H-pyrrolo[2,3-d]pyrimidin-4-yl)-1H-pyrazol-1-yl}-3-cyclopentylpropionitrile (11a) (12 g, 27.7 mmol, 1.0 eq.) in methanol was added 80% hydrazine hydrate (8.7 g, 138 mmol, 5.0 eq.) drop-wise under stirring at room temperature, and heated to reflux for 8 hours. The reaction mixture was concentrated under reduced pressure to evaporate the solvent, and the residue was dissolved in ethyl acetate, washed with water and a saturated brine solution, dried over anhydrous sodium sulfate overnight, and filtrated. The filtrate was concentrated under reduced pressure to afford (R)-3-[3-amino-4-(7H-pyrrolo[2,3-d]pyrimidin-4-yl)-1H-pyrazol-1-yl}-3-cyclopentyl propionitrile (I) (7.7 g, yield: 87%, ee value: 99.8%).

$^1$H-NMR (500 MHz, CDCl$_3$): δ 11.73 (s, 1H), 8.79 (s, 1H), 8.06 (s, 1H), 7.32 (d, J=3.5 Hz, 1H), 6.62 (d, J=3.5 Hz, 1H), 5.03 (s, 2H), 4.05 (td, J=9.5, 3.5 Hz, 1H), 3.12 (dd, J=17.1, 8.9 Hz, 1H), 2.91 (dd, J=17.1, 3.6 Hz, 1H), 2.54 (m, 1H), 1.74 (m, 1H), 1.63 (m, 4H), 1.27 (m, 1H), 1.26 (m, 2H); FIRMS (ESI) calcd. for C$_{17}$H$_{19}$N$_7$ [M+H]$^+$ 322.1775; Found: 322.1783.

Example 2 (3R)-3-{3-amino-4-{7H-pyrrolo[2,3-d]pyrimidin-4-yl}-1H-pyrazol-1-yl}-3-cyclopentylpropionitrile (I)

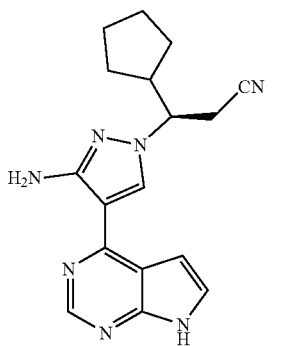

Step A: 2-{7-{[2-(trimethylsilyl)ethoxy]methyl}-7H-pyrrolo[2,3-d]pyrimidin-4-yl}malononitrile (12a)

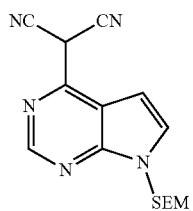

To a 0.5M solution of the compound (2) obtained in Step E of Example 1 (141.9 g, 0.5 mol, 1.0 eq.) in DMF were sequentially added malononitrile (39.7 g, 0.6 mol, 1.2 eq.) and potassium carbonate (207.3 g, 1.5 mol, 3.0 eq.) under stirring at room temperature, heated to 120° C. and stirred for 6 hours at that temperature. The reaction was cooled to room temperature and filtrated, and the filtrate was diluted with purified water and extracted with ethyl acetate. The aqueous layer was adjusted to pH 3.0 with 3M HCl, stirred at 5-15° C. to precipitate crystals, and filtrated. The filter cake was washed with water, and forced air-dried at 50° C. to afford 2-{7-{[2-(trimethylsilyl)ethoxy]methyl}-7H-pyrrolo[2,3-d]pyrimidin-4-yl}malononitrile (12a) (145 g, yield: 92.5%).

$^1$H-NMR (500 MHz, CDCl$_3$): δ 12.87 (brs, 1H), 8.17 (s, 1H), 7.54 (d, J=3.6 Hz, 1H), 6.99 (d, J=3.6 Hz, 1H), 5.54 (s, 2H), 3.51 (t, J=7.9 Hz, 2H), 0.82 (t, J=7.9 Hz, 2H), -0.09 (s, 9H); FIRMS (ESI) calcd. for C$_{15}$H$_{19}$N$_5$OSi [M+H]$^+$ 314.1432; Found: 314.1439.

Step B: 3-amino-2-{7-{[2-(trimethylsilyl)ethoxy]methyl}-7H-pyrrolo[2,3-d]pyrimidin-4-yl}acrylonitrile (13a)

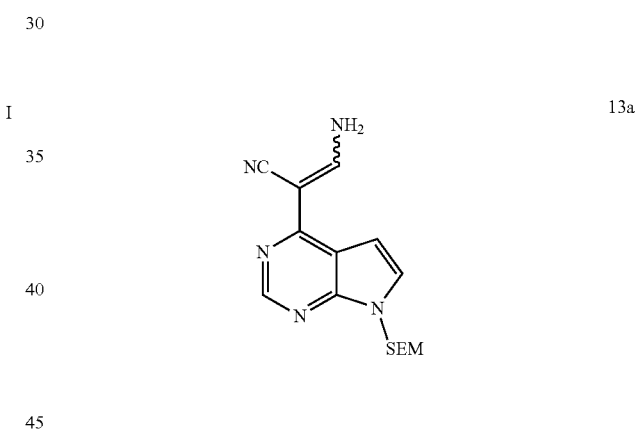

To a 0.3M solution of 2-{7-{[2-(trimethylsilyl)ethoxy]methyl}-7H-pyrrolo[2,3-d]pyrimidin-4-yl}malononitrile (12a) (141 g, 0.45 mol) in DMF was added 5% Pd/C (39.2 g) under stirring at room temperature. The reaction mixture was stirred uniformly and added to a hydrogenation reactor, and stirred for 24 hours under a 1.0 MPa of controlled hydrogen pressure, and then filtrated. Water was added to the filtrate, precipitated crystals, and filtrated. The filter cake was washed with water, and forced air-dried at 45° C. to afford 3-amino-2-{7-{[2-(trimethylsilyl)ethoxy]methyl}-7H-pyrrolo-[2,3-d]pyrimidin-4-yl}acrylonitrile (13a) (136.2 g, yield: 96%).

$^1$H-NMR (500 MHz, CDCl$_3$): M8.62 (s, 1H), 8.50 (s, 1H), 8.25 (s, 1H), 8.07 (s, 1H), 7.59 (d, J=3.4 Hz, 1H), 7.13 (d, J=3.4 Hz, 1H), 5.60 (d, J=16.3 Hz, 2H), 3.50 (t, J=7.9 Hz, 2H), 0.81 (t, J=7.9 Hz, 2H), -0.11 (s, 9H); HRMS (ESI) Cacld. for C$_{15}$H$_{21}$N$_5$OSi [M+H]$^+$ 316.1588; Found: 316.1590.

Step C: (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentylpropanamide (14a)

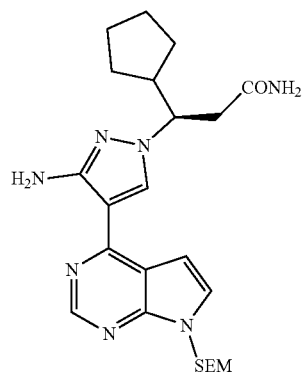

14a

To a 0.5M solution of 3-amino-2-{7-{[2-(trimethylsilyl)ethoxy]methyl}-7H-pyrrolo[2,3-d]pyrimidin-4-yl}acrylonitrile (13a) (101 g, 0.32 mol, 1.0 eq.) in N-methyl pyrrolidone were sequentially added the compound (6) (59.2 g, 0.48 mol, 1.2 eq.) obtained in Step D of Example 1 and N,N-diisopropylethylamine (62 g, 0.48 mol, 1.5 eq.) under stirring at room temperature, and heated to 120° C. and stirred for 12 hours under the protection of nitrogen gas. The reaction was cooled to room temperature, quenched with water, and extracted with ethyl acetate. The ethyl acetate layer was washed with water and a saturated brine solution, dried over anhydrous sodium sulfate, decolored with activated carbon, and filtrated. The filtrate was concentrated under reduced pressure to obtain the sticky residue, which was purified by column chromatography on silica-gel to afford (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentylpropanamide (14a) (89.2 g, yield: 59.4%, ee value: 100.0%).

$^1$H-NMR (500 MHz, CDCl$_3$): δ 8.78 (s, 1H), 7.95 (s, 1H), 7.33 (d, J=3.7 Hz, 1H), 6.67 (d, J=3.7 Hz, 1H), 5.92 (s, 1H), 5.66 (d, J=10.7 Hz, 2H), 5.45 (s, 1H), 4.20 (td, J=10.5, 3.0 Hz, 1H), 3.53 (t, J=8.5 Hz, 2H), 2.99 (dd, J=14.5, 10.9 Hz, 1H), 2.67 (dd, J=14.4, 3.3 Hz, 1H), 1.84 (m, 1H), 1.69 (m, 1H), 1.60 (m, 2H), 1.52 (m, 2H), 1.28 (m, 2H), 1.16 (m, 1H), 0.92 (dd, J=8.9, 7.7 Hz, 2H), −0.05 (s, 9H); HRMS (ESI) Cacld. for C$_{23}$H$_{35}$N$_7$O$_2$Si [M+H]$^+$ 470.2694; Found: 470.2704.

Step D: (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentylpropanamide (9b)

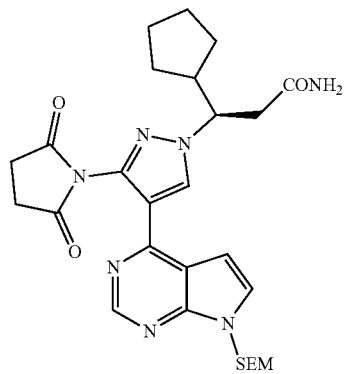

9b

To a 0.2M solution of (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentylpropanamide (14a) (40 g, 85.2 mmol, 1.0 eq.) in toluene was added butanedioic anhydride (11.9 g, 119 mmol, 1.4 eq.) under stirring at room temperature, and heated to reflux for 8 hours under stirring. The reaction was cooled to room temperature, and concentrated under reduced pressure to evaporate solvent, and the residue was dissolved in ethyl acetate, washed with water and a saturated brine solution, dried over anhydrous sodium sulfate and filtrated. The filtrate was concentrated under reduced pressure to afford (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentylpropanamide (9b) (42.8 g, yield: 91.2%). The data was referred to Step K of Example 1. Subsequent steps are the same as Steps L to N of Example 1.

Example 3 (3R)-3-{3-amino-4-{7H-pyrrolo[2,3-d]pyrimidin-4-yl}-1H-pyrazol-1-yl}-3-cyclopentylpropionitrile (I)

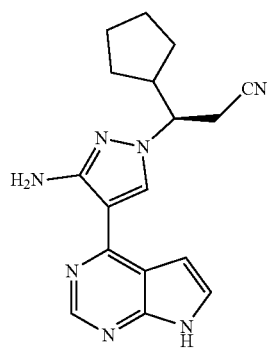

I

Step A: (R)-3-{3-(1,3-dioxoisoindol-2-yl)-4-{7-{[2-(trimethylsilyl)ethoxy]methyl}-7H-pyrrolo[2,3-d]pyrimidin-4-yl}}-1H-pyrazol-1-yl]-3-cyclopentyl-propanamide (9c)

Step B: (R)-3-{3-(1,3-dioxoisoindol-2-yl)-4-{7-{[2-(trimethylsilyl)ethoxy]methyl}-7H-pyrrolo[2,3-d]pyrimidin-4-yl}}-1H-pyrazol-1-yl]-3-cyclopentyl-propionitrile (10c)

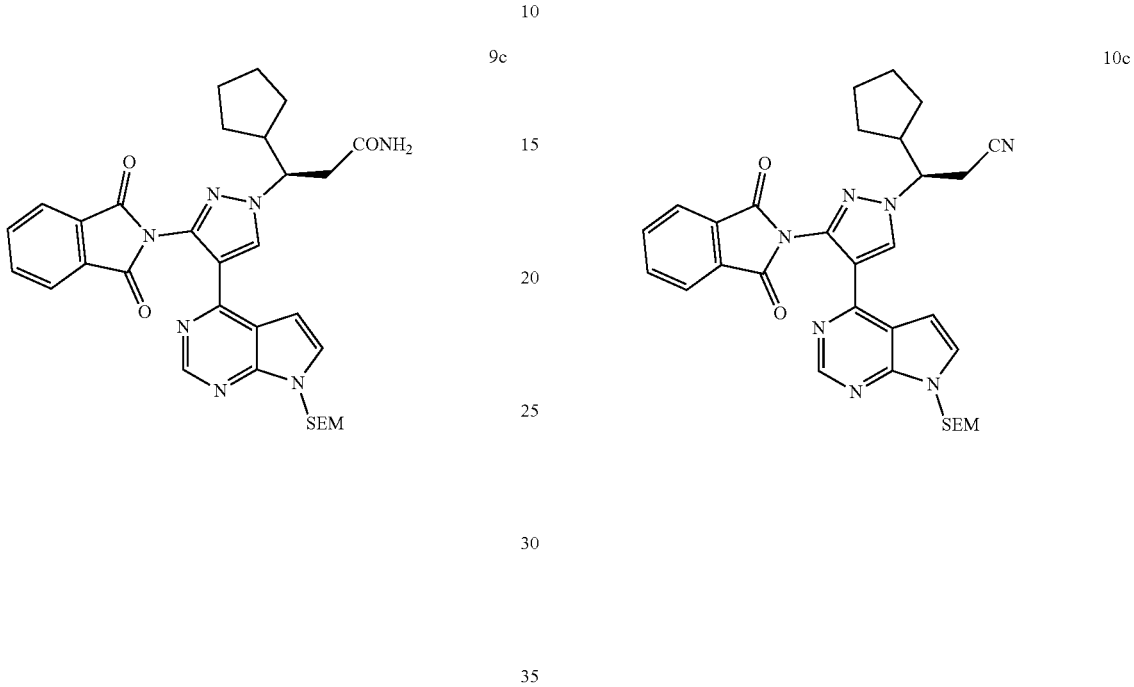

To a 0.15M solution of the compound obtained in Step C of Example 2 (14a) (40 g, 85.2 mmol, 1.0 eq.) in toluene was added phthalic anhydride (15.1 g, 0.1 mol, 1.2 eq.) under stirring at room temperature, heated to reflux for 4 hours, and then cooled to room temperature. The reaction mixture was concentrated under reduced pressure to evaporate the solvent, dissolved in ethyl acetate, washed with a saturated sodium bicarbonate solution, water and a saturated brine solution, dried over anhydrous sodium sulfate, and filtrated. The filtrate was concentrated under reduced pressure to afford (R)-3-{3-(1,3-dioxoisoindol-2-yl)-4-{7-{[2-(trimethylsilyl)ethoxy]methyl}-7H-pyrrolo[2,3-d]pyrimidin-4-yl}}-1H-pyrazol-1-yl]-3-cyclopentylpropanamide (9c) (47.3 g, yield: 92.5%).

To a 0.15M solution of (R)-3-cyclopentyl-3-{3-(1,3-dioxoisoindol-2-yl)-4-{7-{[2-(trimethylsilyl)ethoxy]methyl}-7H-pyrrolo[2,3-d]pyrimidin-4-yl}}-1H-pyrazol-1-yl]propanamide (9c) (45 g, 75 mmol, 1.0 eq.) in dichloromethane was added phosphorus oxychloride (46 g, 0.3 mol, 4.0 eq.) drop-wise in an ice bath under stirring, and stirred for 4 hours at room temperature. The reaction was quenched with water, and layers were separated. The aqueous layer was extracted with dichloromethane, and the organic layer was combined, dried over anhydrous magnesium sulfate, and filtrated. The filtrate was concentrated under reduced pressure to afford (R)-3-{3-(1,3-dioxoisoindol-2-yl)-4-{7-{[2-(trimethylsilyl)ethoxy]methyl}-7H-pyrrolo[2,3-d]pyrimidin-4-yl}}-1H-pyrazol-1-yl]-3-cyclopentylpropionitrile (10c) (40.1 g, yield: 92%).

$^1$H-NMR (500 MHz, CDCl$_3$): δ 8.45 (s, 1H), 8.26 (s, 1H), 7.94 (m, 2H), 7.81 (m, 2H), 7.33 (m, 1H), 6.66 (d, J=2.2 Hz, 1H), 6.08 (s, 1Hs), 5.60 (s, 2H), 5.44 (s, 1H), 4.46 (t, J=10.5 Hz, 1H), 3.50 (t, J=8.4 Hz, 2H), 3.12 (t, J=12.5 Hz, 2H), 2.77 (d, J=13.5 Hz, 1H), 2.59 (m, 1H), 1.93 (m, 1H), 1.73-1.60 (m, 5H), 1.41-1.27 (m, 3H), 0.89 (t, J=8.1 Hz, 2H), −0.06 (s, 9H); FIRMS (ES) Cacld. for C$_{31}$H$_{37}$N$_7$O$_4$Si [M+H]$^+$ 600.2749; Found: 600.2756.

$^1$H-NMR (500 MHz, CDCl$_3$): δ 8.49 (1H, s), 8.38 (s, 1H), 7.94 (m, 2H), 7.80 (m, 2H), 7.34 (d, J=3.7 Hz, 1H), 6.68 (d, J=3.7 Hz, 1H), 5.60 (d, J=3.4 Hz, 2H), 4.36 (m, 1H), 3.50 (t, J=8.1 Hz, 2H), 3.16 (dd, J=17.5, 7.4 Hz, 1H), 3.07 (dd, J=17.5, 4.1 Hz, 1H), 2.85 (s, 1H), 2.69 (m, 1H), 2.01 (m, 1H), 1.76-1.62 (m, 5H), 1.36-1.33 (m, 3H), 0.89 (t, J=8.1 Hz, 2H), −0.06 (s, 9H); FIRMS (ESI) Cacld. for C$_{31}$H$_{35}$N$_7$O$_3$Si [M+H]$^+$ 582.2643; Found: 582.2653.

Step C: (R)-3-{3-(1,3-dioxoisoindol-2-yl)-4-[7-(hydroxymethyl)-7H-pyrrolo[2,3-d]pyrimidin-4-yl]-1H-pyrazol-1-yl]-3-cyclopentyl propionitrile (11b)

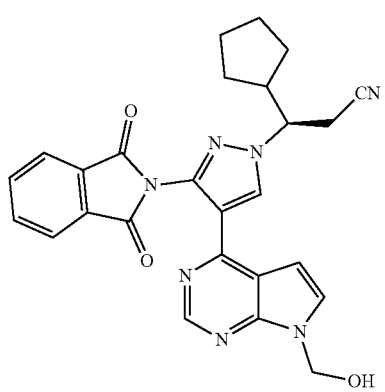

To a 0.15M solution of (R)-3-{3-(1,3-dioxoisoindol-2-yl)-4-{7-{[2-(trimethylsilyl)ethoxy]methyl}-7H-pyrrolo[2,3-d]pyrimidin-4-yl]}-1H-pyrazol-1-yl]-3-cyclopentylpropionitrile (10c) (37.8 g, 65 mmol, 1.0 eq.) in dichloromethane was added 47% boron trifluoride solution in diethyl ether (59 g, 0.2 mol, 3.0 eq.) drop-wise in an ice bath under stirring, and then stirred for 4 hours at room temperature. The reaction mixture was concentrated under reduced pressure to evaporate the solvent, and the resulting residue was dissolved in ethyl acetate and adjusted to pH6~7 with 10% NaOH solution. The ethyl acetate layer was washed with water and a saturated brine solution, dried over anhydrous sodium sulfate, and filtrated. The filtrate was concentrated under reduced pressure to afford (R)-3-{3-(1,3-dioxoisoindol-2-yl)-4-[7-(hydroxymethyl)-7H-pyrrolo[2,3-d]pyrimidin-4-yl]-1H-pyrazol-1-yl]-3-cyclopentylpropionitrile (11b) (26.9 g, yield: 86%).

$^1$H-NMR (500 MHz, CDCl$_3$): δ 8.30 (s, 1H), 8.23 (s, 1H), 7.91 (m, 2H), 7.77 (m, 2H), 7.21 (d, J=2.4 Hz, 1H), 6.49 (d, J=2.4 Hz, 1H), 5.54 (q, J=10.8 Hz, 2H), 4.34 (m, 1H), 3.17 (dd, J=17.2, 8.0 Hz, 2H), 3.03 (dd, J=17.2, 2.8 Hz, 1H), 2.62 (m, 1H), 1.95 (m, 1H), 1.71-1.56 (m, 6H), 1.33-1.24 (m, 4H); HRMS (ESI) Cacld. for C$_{26}$H$_{23}$N$_7$O$_3$ [M+H]$^+$ 482.1935; Found: 482.1947.

Step D: (R)-3-amino-4-(7H-pyrrolo[2,3-d]pyrimidin-4-yl)-1H-pyrazol-1-yl}-3-cyclopentyl propionitrile (I)

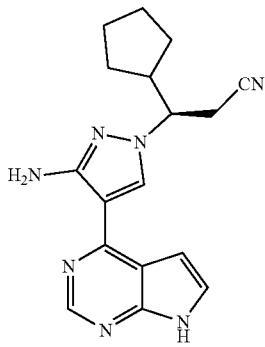

To a 0.2M solution of (R)-3-[3-(2,5-dioxoisoindol-2-yl)-4-(7-hydroxymethyl)-7H-pyrrolo[2,3-d]pyrimidin-4-yl)-1H-pyrazol-1-yl]-3-cyclopentylpropionitrile (11b) (24.1 g, 50 mmol, 1.0 eq.) in methanol was added 80% hydrazine hydrate (15.6 g, 0.25 mmol, 5.0 eq.) drop-wise under stirring at room temperature, and then heated to reflux for 4 hours. The reaction mixture was concentrated under reduced pressure to evaporate the solvent, and the residue was dissolved in ethyl acetate, washed with water and a saturated brine solution, dried over anhydrous sodium sulfate, and filtrated. The filtrate was concentrated under reduced pressure to afford (R)-3-[3-amino-4-(7H-pyrrolo[2,3-d]pyrimidin-4-yl)-1H-pyrazol-1-yl}-3-cyclopentyl propionitrile (I) (14.7 g, yield: 91.4%, ee value: 100.0%). The data was referred to Step N in Example 1.

What is claimed is:

1. A method for preparing a compound of formula I, comprising reacting a compound of formula A with a compound of formula 6 or a salt thereof to obtain a compound of formula 7 or a compound of formula 14, and preparing the compound of formula I from the compound of formula 7 or the compound of formula 14:

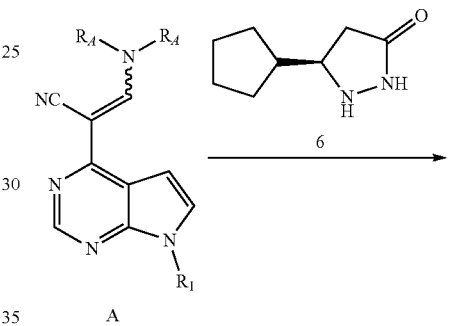

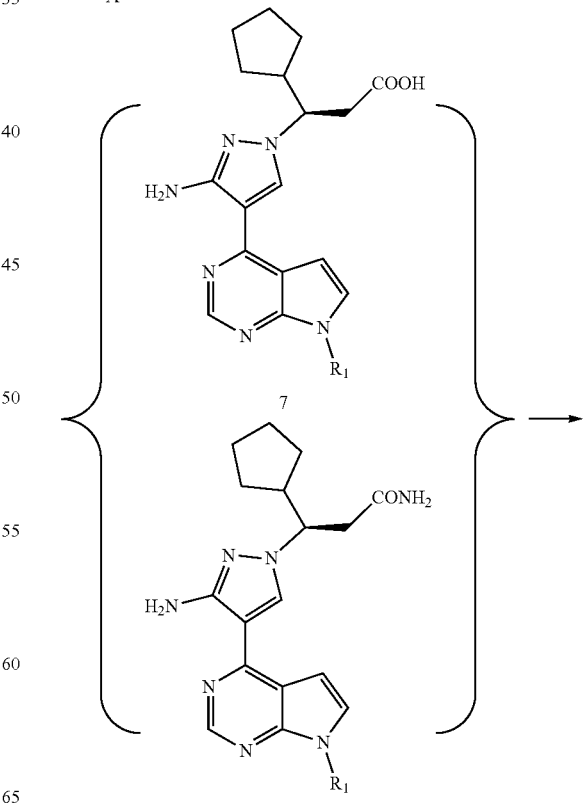

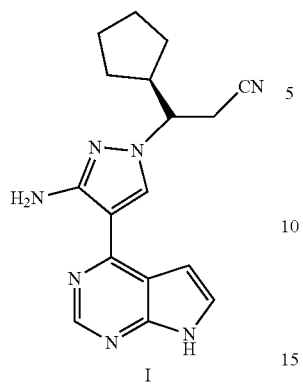

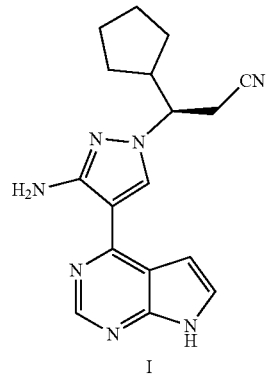

wherein R¹ is selected from the group consisting of H and an amino-protecting group; and $R_A$ is selected from the group consisting of H and $CH_3$.

2. The method of claim 1, comprising reacting a compound of formula 5 with the compound of formula 6 or a salt thereof to obtain the compound of formula 7, and preparing the compound of formula I from the compound of formula 7:

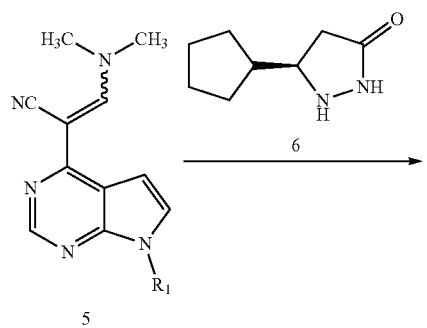

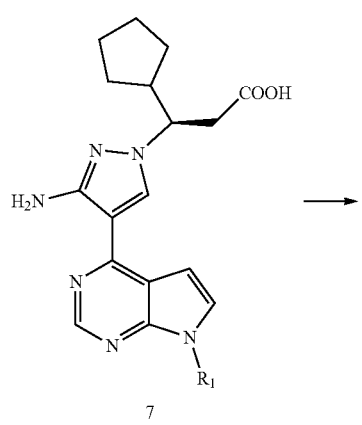

wherein $R_1$ is selected from the group consisting of H and an amino-protecting group.

3. The method of claim 2, wherein the process for preparing the compound of formula I from the compound of formula 7 comprises: a) a reaction of converting carboxy group into amido group, b) a reaction of converting amido group into cyano group, c) a reaction of linking amino group on a pyrazole ring with a protecting group, d) a reaction of removing the protective group of amino group on the pyrazole ring, and/or e) a reaction of removing $R_1$.

4. The method of claim 2, wherein $R_1$ in the compound of formula 7 is an amino-protecting group, and the process for preparing the compound of formula I from the compound of formula 7 comprises the following steps: (1) linking amino group on a pyrazole ring of the compound of formula 7 with a protecting group; (2) converting carboxy group of the compound obtained from step (1) into amido group; (3) converting amido group of the compound obtained from step (2) into cyano group; (4) removing the protective group of amino group on the pyrazole ring of the compound obtained from step (3), and (5) removing $R_1$ prior to step (1), after step (1) but prior to step (2), after step (2) but prior to step (3), after step (3) but prior to step (4), after step (4), or at the same time as step (4); or $R_1$ in the compound of formula 7 is H, and the process for preparing the compound of formula I from the compound of formula 7 comprises the following steps: (1) linking amino group on a pyrazole ring of the compound of formula 7 with a protecting group; (2) converting carboxy group of the compound obtained from step (1) into amido group; (3) converting amido group of the compound obtained from step (2) into cyano group; and (4) removing the protective group of amino group on the pyrazole ring of the compound obtained from step (3).

5. The method of claim 1, comprising reacting a compound of formula 13 with a compound of formula 6 or a salt thereof to obtain a compound of formula 14, and preparing the compound of formula I from the compound of formula 14:

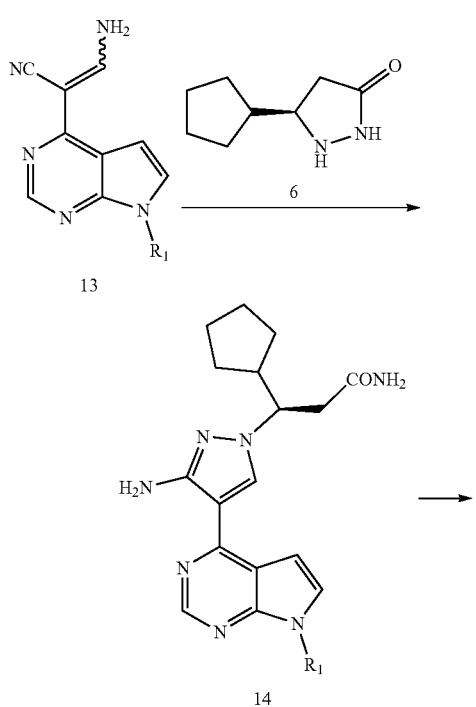

wherein R₁ is selected from the group consisting of H and an amino-protecting group.

6. The method of claim 5, wherein the process for preparing the compound of formula I from the compound of formula 14 comprises f) a reaction of converting amido group into cyano group, g) a reaction of linking amino group on a pyrazole ring with a protecting group, h) a reaction of removing the protective group of amino group on the pyrazole ring, and/or i) a reaction of removing R₁.

7. The method of claim 5, wherein R₁ in the compound of formula 14 is an amino-protecting group, and the process for preparing the compound of formula I from the compound of formula 14 comprises the following steps: (1) linking amino group on a pyrazole ring of the compound of formula 14 with a protecting group; (2) converting amido group of the compound obtained from step (1) into cyano group; (3) removing the protective group of amino group on the pyrazole ring of the compound obtained from step (2), and (4) removing R₁ prior to step (1), after step (1) but prior to step (2), after step (2) but prior to step (3), after step (3), or at the same time as step (3); or R₁ in the compound of formula 14 is H, and the process for preparing the compound of formula I from the compound of formula 14 comprises the following steps: (1) linking amino group on a pyrazole ring of the compound of formula 14 with a protecting group; (2) converting amido group of the compound obtained from step (1) into cyano group; and (3) removing the protective group of amino group on the pyrazole ring of the compound obtained from step (2).

8. The method of claim 1, wherein the amino-protecting groups is selected from the group consisting of hydroxymethyl, benzyloxycarbonyl, 2,2,2-trichloroethoxycarbonyl, 2-(trimethylsilyl)ethoxycarbonyl, 2-(4-trifluoromethylbenzenesulfonyl)ethoxycarbonyl, tert-butyloxycarbonyl, 1-adamantyloxocarbonyl, 2-adamantylcarbonyl, 2,4-dimethylpent-3-yloxycarbonyl, cyclohexyloxycarbonyl, 1,1-dimethyl-2,2,2-trichloroethoxycarbonyl, vinyl, 2-chloroethyl, 2-benzenesulfonylethyl, p-nitrobenzenesulfonyl, p-methylbenzenesulfonyl, benzenesulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butyloxymethyl, benzyloxymethyl, 2-tetrahydropyranyl, tri($C_{1-4}$ alkyl)silyl, 1,1-diethoxymethyl, 2-(trimethylsilyl)ethoxymethyl, and N-pivaloyloxymethyl.

9. A method for preparing the compound of formula 7 of claim 1, comprising reacting a compound of formula 5 with a compound of formula 6 or a salt thereof to obtain the compound of formula 7:

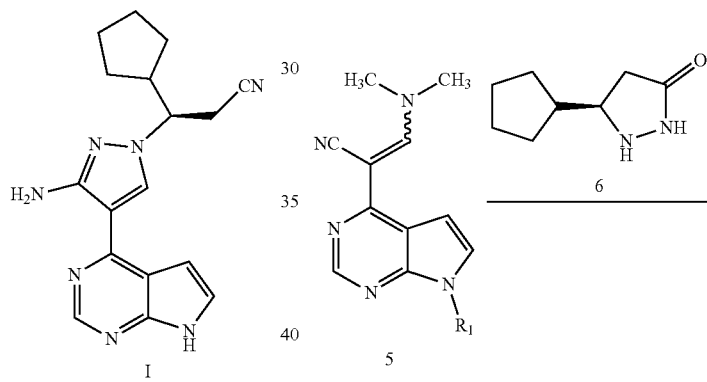

wherein R₁ is selected from the group consisting of H and an amino-protecting group.

10. The method of claim 9, wherein the amino-protecting groups is selected from the group consisting of hydroxymethyl, benzyloxycarbonyl, 2,2,2-trichloroethoxycarbonyl, 2-(trimethylsilyl)ethoxycarbonyl, 2-(4-trifluoromethylbenzenesulfonyl)ethoxycarbonyl, tert-butyloxycarbonyl, 1-adamantyloxocarbonyl, 2-adamantylcarbonyl, 2,4-dimethylpent-3-yloxycarbonyl, cyclohexyloxycarbonyl, 1,1- dimethyl-2,2,2-trichloroethoxycarbonyl, vinyl, 2-chloroethyl, 2-benzenesulfonylethyl, p-nitrobenzenesulfonyl, p-methylbenzenesulfonyl, benzenesulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butyloxymethyl, benzyloxymethyl, 2-tetrahydropyranyl, tri($C_{1-4}$ alkyl)silyl, 1,1-diethoxymethyl, 2-(trimethylsilyl)ethoxymethyl, and N-pivaloyloxymethyl.

11. A method for preparing the compound of formula 14 of claim 1, comprising reacting a compound of formula 13 with a compound of formula 6 or a salt thereof to obtain the compound of formula 14:

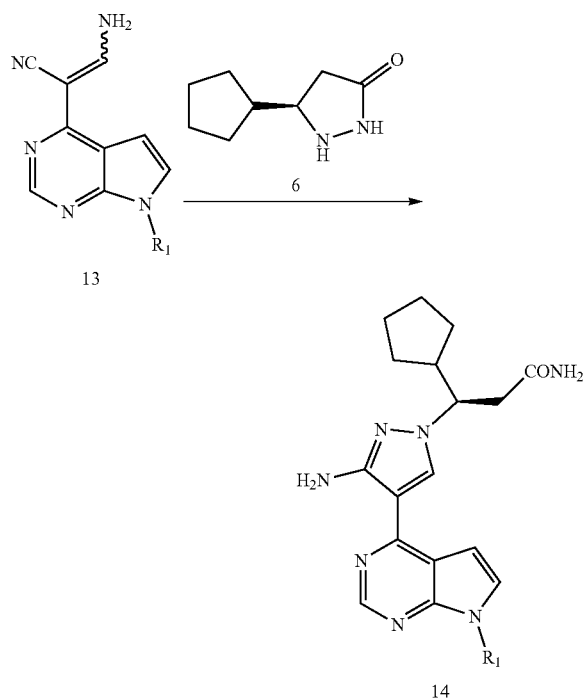

wherein $R_1$ is selected from the group consisting of H and an amino-protecting group.

12. The method of claim 11, wherein the amino-protecting groups is selected from the group consisting of hydroxymethyl, benzyloxycarbonyl, 2,2,2-trichloroethoxycarbonyl, 2-(trimethylsilyl)ethoxycarbonyl, 2-(4-trifluoromethylbenzenesulfonyl)ethoxycarbonyl, tert-butyloxycarbonyl, 1-adamantyloxocarbonyl, 2-adamantylcarbonyl, 2,4-dimethylpent-3-yloxycarbonyl, cyclohexyloxycarbonyl, 1,1-dimethyl-2,2,2-trichloroethoxycarbonyl, vinyl, 2-chloroethyl, 2-benzenesulfonylethyl, p-nitrobenzenesulfonyl, p-methylbenzenesulfonyl, benzenesulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butyloxymethyl, benzyloxymethyl, 2-tetrahydropyranyl, tri($C_{1-4}$ alkyl)silyl, 1,1-diethoxymethyl, 2-(trimethylsilyl)ethoxymethyl, and N-pivaloyloxymethyl.

13. A compound of formula 13:

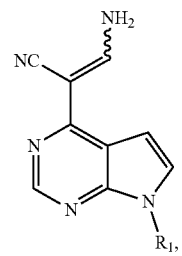

wherein $R_1$ is selected from the group consisting of H and an amino-protecting group.

14. The compound of claim 13, wherein the amino-protecting groups is selected from the group consisting of hydroxymethyl, benzyloxycarbonyl, 2,2,2-trichloroethoxycarbonyl, 2-(trimethylsilyl)ethoxycarbonyl, 2-(4-trifluoromethylbenzenesulfonyl)ethoxycarbonyl, tert-butyloxycarbonyl, 1-adamantyloxocarbonyl, 2-adamantylcarbonyl, 2,4-dimethylpent-3-yloxycarbonyl, cyclohexyloxycarbonyl, 1,1-dimethyl-2,2,2-trichloroethoxycarbonyl, vinyl, 2-chloroethyl, 2-benzenesulfonylethyl, p-nitrobenzenesulfonyl, p-methylbenzenesulfonyl, benzenesulfonyl, methanesulfonyl, allyl, benzyl, 2-nitrobenzyl, 4-nitrobenzyl, diphenyl-4-pyridylmethyl, N',N'-dimethylhydrazino, methoxymethyl, tert-butyloxymethyl, benzyloxymethyl, 2-tetrahydropyranyl, tri($C_{1-4}$ alkyl)silyl, 1,1-diethoxymethyl, 2-(trimethylsilyl)ethoxymethyl, and N-pivaloyloxymethyl.

15. The method of claim 8, wherein the amino-protecting groups is selected from the group consisting of hydroxymethyl, 2-(trimethylsilyl)ethoxymethyl, N-pivaloyloxymethyl, p-nitrobenzenesulfonyl, p-methylbenzenesulfonyl, benzenesulfonyl, methanesulfonyl, and benzyl.

16. The method of claim 8, wherein the amino-protecting groups is hydroxymethyl or 2-(trimethylsilyl)ethoxymethyl.

17. The method of claim 10, wherein the amino-protecting groups is selected from the group consisting of hydroxymethyl, 2-(trimethylsilyl)ethoxymethyl, N-pivaloyloxymethyl, p-nitrobenzenesulfonyl, p-methylbenzenesulfonyl, benzenesulfonyl, methanesulfonyl, and benzyl.

18. The method of claim 12, wherein the amino-protecting groups is selected from the group consisting of hydroxymethyl, 2-(trimethylsilyl)ethoxymethyl, N-pivaloyloxymethyl, p-nitrobenzenesulfonyl, p-methylbenzenesulfonyl, benzenesulfonyl, methanesulfonyl, and benzyl.

19. The compound of claim 14, wherein the amino-protecting groups is selected from the group consisting of hydroxymethyl, 2-(trimethylsilyl)ethoxymethyl, N-pivaloyloxymethyl, p-nitrobenzenesulfonyl, p-methylbenzenesulfonyl, benzenesulfonyl, methanesulfonyl, and benzyl.

20. The compound of claim 14, wherein the amino-protecting groups is hydroxymethyl and 2-(trimethylsilyl)ethoxymethyl.

* * * * *